(12) United States Patent
Tachibana et al.

(10) Patent No.: US 11,307,497 B2
(45) Date of Patent: Apr. 19, 2022

(54) COMPOUND, COMPOSITION FOR FORMING ORGANIC FILM, SUBSTRATE FOR MANUFACTURING SEMICONDUCTOR APPARATUS, METHOD FOR FORMING ORGANIC FILM, AND PATTERNING PROCESS

(71) Applicant: SHIN-ETSU CHEMICAL CO., LTD., Tokyo (JP)

(72) Inventors: Seiichiro Tachibana, Joetsu (JP); Takeru Watanabe, Joetsu (JP); Keisuke Niida, Joetsu (JP); Hiroko Nagai, Joetsu (JP); Takashi Sawamura, Joetsu (JP); Tsutomu Ogihara, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 237 days.

(21) Appl. No.: 16/293,150

(22) Filed: Mar. 5, 2019

(65) Prior Publication Data
US 2019/0300498 A1 Oct. 3, 2019

(30) Foreign Application Priority Data

Mar. 28, 2018 (JP) .............................. JP2018-062335

(51) Int. Cl.
*G03F 7/025* (2006.01)
*G03F 7/11* (2006.01)
(Continued)

(52) U.S. Cl.
CPC .............. *G03F 7/025* (2013.01); *C07C 15/56* (2013.01); *C07D 335/12* (2013.01); *C08F 38/00* (2013.01);
(Continued)

(58) Field of Classification Search
CPC . G03F 7/025; G03F 7/11; C07C 15/58; C07C 35/38; C07C 33/04
See application file for complete search history.

(56) References Cited

U.S. PATENT DOCUMENTS 4,100,138 A * 7/1978 Bilow ................. C08G 73/101
428/435
9,182,671 B2 * 11/2015 Nakafuji ............... G03F 7/0384
(Continued)

FOREIGN PATENT DOCUMENTS

JP H08-13400 A 1/1996
JP H08-134000 A 5/1996
(Continued)

OTHER PUBLICATIONS

Dec. 30, 2020 Office Action in Korean Patent Application No. 10-2019-0035328.
(Continued)

*Primary Examiner* — John S Chu
(74) *Attorney, Agent, or Firm* — Oliff PLC

(57) ABSTRACT

A compound including two or more partial structures shown by the following general formula (1-1) in the molecule,

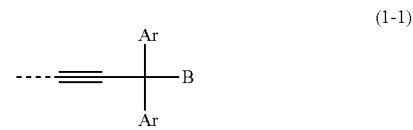

(1-1)

wherein each Ar independently represents an aromatic ring optionally having a substituent or an aromatic ring that contains at least one nitrogen atom optionally having a substituent, and two Ars are optionally bonded with each (Continued)

other to form a ring structure; the broken line represents a bond with an organic group; B represents an anionic leaving group that is capable of forming a reactive cation due to effect of either or both of heat and acid. This provides a compound that is capable of curing under the film forming conditions in air or an inert gas without forming byproducts, and forming an organic under layer film that has good dry etching durability during substrate processing not only excellent characteristics of gap filling and planarizing a pattern formed on a substrate.

17 Claims, 2 Drawing Sheets

(51) Int. Cl.
| | |
|---|---|
| G03F 7/09 | (2006.01) |
| C07D 335/12 | (2006.01) |
| H01L 21/027 | (2006.01) |
| H01L 21/311 | (2006.01) |
| C08F 38/00 | (2006.01) |
| C07C 15/56 | (2006.01) |
| C07C 41/01 | (2006.01) |
| C07C 215/46 | (2006.01) |

(52) U.S. Cl.
CPC .............. $G03F\ 7/091$ (2013.01); $G03F\ 7/094$ (2013.01); $G03F\ 7/11$ (2013.01); $H01L\ 21/0271$ (2013.01); $H01L\ 21/31138$ (2013.01); $C07C\ 41/01$ (2013.01); $C07C\ 215/46$ (2013.01)

(56) References Cited

U.S. PATENT DOCUMENTS

| | | | |
|---|---|---|---|
| 10,604,618 B2* | 3/2020 | Tachibana | C08G 61/02 |
| 11,022,882 B2* | 6/2021 | Tachibana | G03F 7/025 |
| 2002/0106909 A1 | 8/2002 | Kato et al. | |
| 2005/0255712 A1 | 11/2005 | Kato et al. | |
| 2006/0019195 A1 | 1/2006 | Hatakeyama et al. | |
| 2006/0204891 A1 | 9/2006 | Hatakeyama | |
| 2009/0274978 A1 | 11/2009 | Ohashi et al. | |
| 2010/0099044 A1 | 4/2010 | Hatakeyama et al. | |
| 2013/0302990 A1 | 11/2013 | Watanabe et al. | |
| 2013/0310514 A1 | 11/2013 | Minegishi et al. | |
| 2016/0085152 A1 | 3/2016 | Nakafuji et al. | |
| 2017/0184968 A1 | 6/2017 | Kori et al. | |
| 2017/0184978 A1 | 6/2017 | Tanitsu et al. | |
| 2017/0199457 A1 | 7/2017 | Hatakeyama et al. | |

FOREIGN PATENT DOCUMENTS

| | | |
|---|---|---|
| JP | 2002-334869 A | 11/2002 |
| JP | 2005-128509 A | 5/2005 |
| JP | 2006-285095 A | 10/2006 |
| JP | 2006-293298 A | 10/2006 |
| JP | 2007-199653 A | 8/2007 |
| JP | 2009-269953 A | 11/2009 |
| JP | 2010-122656 A | 6/2010 |
| JP | 2010-181605 A | 8/2010 |
| JP | 2012-215842 A | 11/2012 |
| JP | 2013-151465 A | 8/2013 |
| JP | 2013-253227 A | 12/2013 |
| JP | 2016-044272 A | 4/2016 |
| JP | 2016-060886 A | 4/2016 |
| JP | 2017-119671 A | 7/2017 |
| TW | 201509875 A | 3/2015 |
| TW | 201732438 A | 9/2017 |
| TW | 201734649 A | 10/2017 |
| WO | 2004/066377 A1 | 8/2004 |
| WO | 2014/208324 A1 | 12/2014 |

OTHER PUBLICATIONS

CAS Registry No. 1883451-66-8, Published Mar. 15, 2016 (Created from L10 in Project "Untitled 34").
Feb. 16, 2021 Office Action issued iin Japanese Patent Application No. 2018-062335.
Angew. Int. Ed. Engl., 1996, vol. 35, No. 17, pp. 1956-1959.
CrystEngComm, 2015, vol. 17, No. 43, pp. 8332-8338.
Tetrahedron, 2001, vol. 57, pp. 3761-3767.
Chemische Berichte, 1960, vol. 93, pp. 1870-1877.
Bulletin of the Chemical Society of Japan, 2005, vol. 78, No. 12, pp. 2188-2208.
Chemische Berichte, 1963, vol. 96, pp. 1221-1228.
CrystEngComm, 2008, vol. 10, No. 3, pp. 322-326.
Studies in Organic Chemistry, 1986, Vo.25 (New Syth. Methodol. Funct. Interesting Compd.), pp. 335-348.
Journal of Inclusion Phenomena and Macrocyclic Chemistry, 2003, vol. 47, Nos. 3-4, pp. 113-121.
Nov. 13, 2019 Office Action issued in Taiwanese Patent Application No. 108110200.
Sep. 6, 2019 Extended European Search Report in European Patent Application No. 19162699.3.
Oct. 26, 2021 Office Action issued in Chinese Application No. 201910242725.4.

* cited by examiner

[FIG.1]
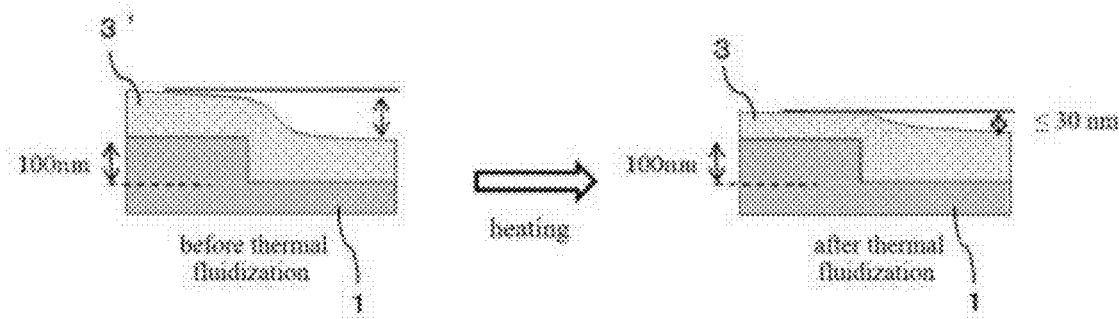
[FIG.2]
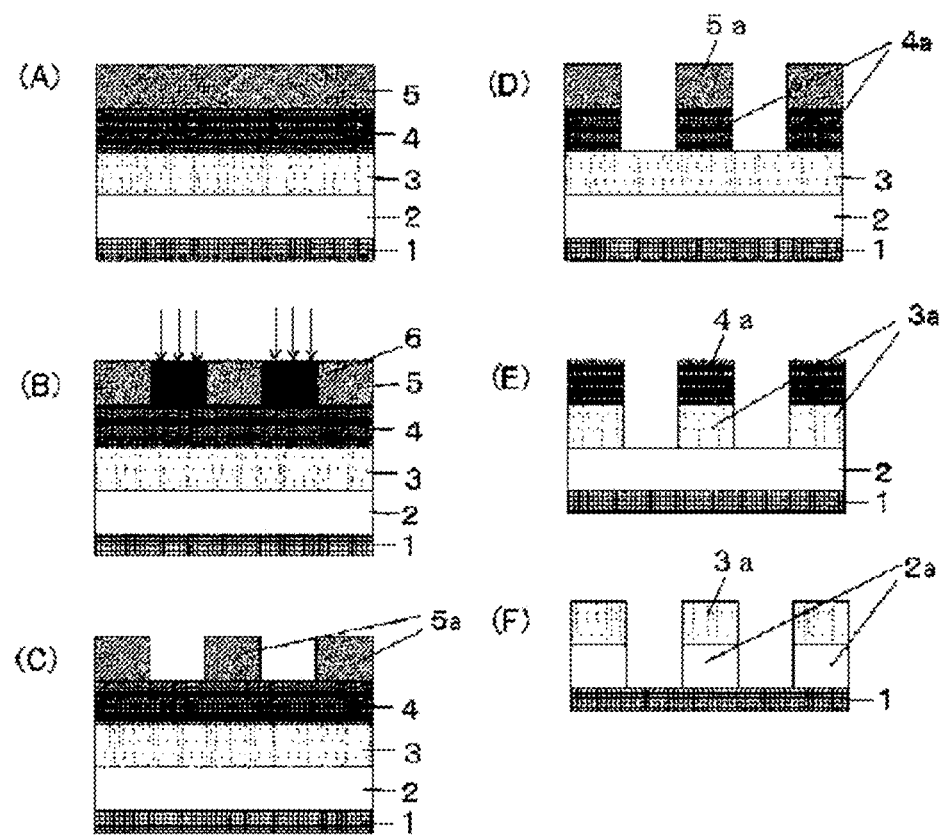

[FIG.3]
(G)
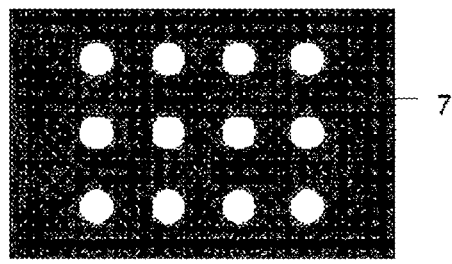
(H)
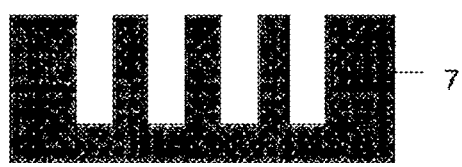
(I)
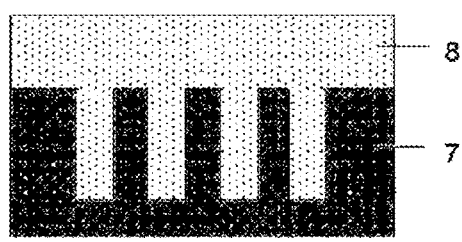
[FIG.4]
(J)
(K)
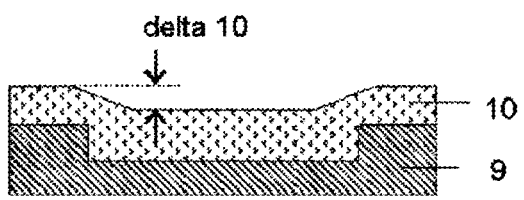

COMPOUND, COMPOSITION FOR FORMING ORGANIC FILM, SUBSTRATE FOR MANUFACTURING SEMICONDUCTOR APPARATUS, METHOD FOR FORMING ORGANIC FILM, AND PATTERNING PROCESS

TECHNICAL FIELD

The present invention relates to a compound, a composition for forming an organic film used in a process for producing a semiconductor device and so on, as well as a substrate for manufacturing a semiconductor apparatus, a method for forming an organic film, and a patterning process using the composition.

BACKGROUND ART

Semiconductor devices have been highly integrated and advanced in processing speed by shifting the wavelength of a light source shorter to attain a finer pattern size in lithography technologies using a light exposure (photolithography) as common arts. In order to form such a fine circuit pattern on a semiconductor device substrate (a substrate to be processed), the substrate is usually processed by dry etching using a photoresist film having a formed pattern as an etching mask. Practically, however, there is no dry etching method having a complete etching selectivity between the photoresist film and the substrate to be processed. Accordingly, substrate processing by a multilayer resist process has been commonly used recently. In this method, a middle layer film having a different etching selectivity from a photoresist film (hereinafter, a resist upper layer film) is set between the resist upper layer film and a substrate to be processed, and a pattern is obtained in the resist upper layer film, and subsequently the pattern is transferred to the middle layer film by dry etching using the resist upper layer film pattern as a dry etching mask, and the pattern is further transferred to the substrate to be processed by dry etching using the middle layer film as a dry etching mask.

One of the multilayer resist processes is a three-layer resist process, which can be performed by using a conventional resist composition that is used in a single layer resist process. In this process, an organic under layer film material composed of a composition containing an organic resin is applied onto a substrate to be processed and is baked to form an organic under layer film (hereinafter, an organic film), a resist middle layer film material composed of a silicon-containing resin composition is applied thereto and is baked to form a silicon-containing film (hereinafter, a silicon middle layer film), and a conventional resist upper layer is formed thereon. After patterning the resist upper layer film, the resist upper layer film pattern can be transferred to the silicon middle layer film by dry etching with a fluorine-base gas plasma since organic resist upper layer films have excellent etching selectivity to silicon middle layer films. This method makes it possible to easily transfer a pattern to a silicon middle layer film even in the use of a resist upper layer film without having a sufficient film thickness for directly processing a substrate to be processed or a resist upper layer film without having a sufficient dry etching durability for processing a substrate to be processed since the silicon middle layer film usually has a film thickness equal to or less than that of the resist upper layer film. The pattern can be transferred to the organic under layer film that has sufficient dry etching durability for substrate processing by transferring the pattern to the organic under layer film by dry etching with an oxygen base or hydrogen base gas plasma using the silicon middle layer film having the pattern transferred thereto as a dry etching mask. This organic under layer film pattern having the pattern transferred thereto can be transferred to a substrate by dry etching by using a fluorine base gas or a chlorine base gas.

On the other hand, the attempt to produce smaller pattern sizes in production processes of semiconductor devices is approaching the inherent limit due to the wavelength of a light source for photolithography. Accordingly, higher integration of semiconductor devices have been investigated recently without depending on smaller pattern sizes. In one of these methods, semiconductor devices with complicated structures have been investigated including a multi gate structure and a gate all-around, and a part of them have been put to practical use already. When these structures are formed by a multilayer resist process, it is possible to apply an organic film material that is capable of planarization by gap filling a minute pattern formed on a substrate to be processed such as a hole, a trench, and a fin with the organic film material without a void, or planarization by filling a step or a pattern dense portion and no pattern region with the organic film material. Such an organic film material is used for forming a planar organic under layer film surface on a stepped substrate to decrease fluctuation of a film thickness of a silicon middle layer film or a resist upper layer film formed thereon, thereby making it possible to avoid the deterioration of focus tolerance in photolithography or a margin in the subsequent processing step of a substrate to be processed. This makes it possible to produce semiconductor devices in a good yield. On the other hand, it is difficult to produce semiconductor devices in a good yield by a single layer resist process since it requires an upper layer resist film to have thicker film thickness for gap filling a stepped or patterned substrate to be processed, thereby causing lower tolerance for pattern forming in exposure such as pattern collapse after exposure and development as well as degradation of a pattern profile due to reflection from a substrate in exposure.

As a method for next-generation semiconductor devices to achieve higher processing speed, investigations have been undertaken on new materials that have high electron mobility using strained silicon and gallium-arsenic etc. or fine materials such as an ultrathin film polysilicon controlled at the angstrom level. When such a new fine material is applied to a substrate to be processed, however, the material can be corroded with oxygen in air atmosphere under conditions in forming a planar film using the organic under layer film material as described above, for example, the film forming conditions of 300° C. or more in air atmosphere. This risks the semiconductor device to fail to attain higher processing speed as it is designed, and fail to attain the yield that can be managed as industrial manufacturing. Accordingly, it is expected that an organic under layer material can form a film even in an inert gas and does not form a byproduct to contaminate a manufacturing device of a semiconductor apparatus in the curing reaction in order to avoid lowering of the yield due to corrosion of a substrate with air under the conditions of higher temperature.

As a material for forming an organic film for a multilayer resist process, condensation resins have been known in which a carbonyl compound such as ketones and aldehydes or an aromatic alcohol is used as a condensation agent to a phenolic or naphtholic compound. Illustrative examples thereof include fluorene bisphenol novolak resins described in Patent Literature 1, bisphenol compounds and novolak resins thereof described in Patent Literature 2, novolak resins of adamantanephenol compounds described in Patent Literature 3, and bisnaphthol compounds and novolak resins thereof described in Patent Literature 4. These materials are formed into a film that has resistance to solvents for the coating film material used in the subsequent step by crosslinking thereof with a methylol compound as a crosslinking agent or curing function due to crosslinking reaction including oxidation of the aromatic ring at the α-position by an effect of oxygen in air atmosphere, followed by condensation.

Additionally, Patent Literatures 5 to 10 have been known, in the material of which has a triple bond applied as a group for intermolecular crosslinking of a curable resin. In these materials, cured films with solvent resistance are formed also by crosslinking caused by polymerization of the triple bonds not only crosslinking due to the methylol. These material for forming an organic film, however, has insufficient characteristics of gap filling and planarizing a pattern formed on a substrate.

CITATION LIST

Patent Literature

PATENT LITERATURE 1: Japanese Patent Laid-Open Publication (Kokai) No. 2005-128509
PATENT LITERATURE 2: Japanese Patent Laid-Open Publication (Kokai) No. 2006-293298
PATENT LITERATURE 3: Japanese Patent Laid-Open Publication (Kokai) No. 2006-285095
PATENT LITERATURE 4: Japanese Patent Laid-Open Publication (Kokai) No. 2010-122656
PATENT LITERATURE 5: Japanese Patent Laid-Open Publication (Kokai) No. 2010-181605
PATENT LITERATURE 6: WO 2014-208324
PATENT LITERATURE 7: Japanese Patent Laid-Open Publication (Kokai) No. 2012-215842
PATENT LITERATURE 8: Japanese Patent Laid-Open Publication (Kokai) No. 2016-044272
PATENT LITERATURE 9: Japanese Patent Laid-Open Publication (Kokai) No. 2016-060886
PATENT LITERATURE 10: Japanese Patent Laid-Open Publication (Kokai) No. 2017-119671

SUMMARY OF INVENTION

Technical Problem

The present invention was accomplished in view of the above-described circumstances. It is an object of the present invention to provide a compound that is capable of curing under the film forming conditions that is not only in air but also in an inert gas without forming byproducts, thereby forming an organic under layer film that has good dry etching durability during substrate processing not only excels in heat resistance and characteristics of gap filling and planarizing a pattern formed on a substrate. The present invention also provides a composition for forming an organic film, a substrate for manufacturing a semiconductor apparatus, a method for forming an organic film, and a patterning process using the compound.

Solution to Problem

To solve the above problems, the present invention provides a compound comprising two or more partial structures shown by the following general formula (1-1) in the molecule,

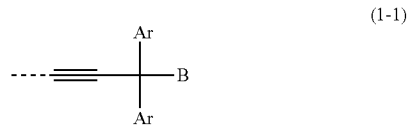

wherein each Ar independently represents an aromatic ring optionally having a substituent or an aromatic ring that contains at least one nitrogen atom optionally having a substituent, and two Ars are optionally bonded with each other to form a ring structure; a broken line represents a bond with an organic group; B represents an anionic leaving group that is capable of forming a reactive cation due to effect of either or both of heat and acid.

The compound like this is capable of curing under the film forming conditions that is not only in air but also in an inert gas without forming byproducts, thereby forming an organic under layer film that has good dry etching durability in substrate processing not only excels in heat resistance and characteristics of gap filling and planarizing a pattern formed on a substrate.

In this case, the above compound is preferably a compound shown by the following general formula (1-2),

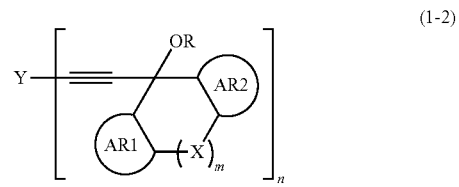

wherein AR1 and AR2 each represent a benzene ring, a naphthalene ring, or a pyridine ring optionally having an alkoxy group, an alkenyloxy group, or an aryloxy group having 1 to 30 carbon atoms; "m" is 0 or 1; when m=0, the aromatic rings of AR1 and AR2 do not form a bridged structure with each other, when m=1, AR1 and AR2 form a bridged structure in which the aromatic rings of AR1 and AR2 are bonded with each other through X; X represents a single bond or any of groups shown by the following formulae (3);

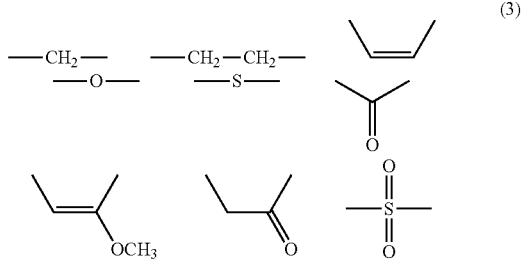

Y represents an n-valent organic group having 1 to 30 carbon atoms in which n=2 to 4 or an organic group-containing polymer having n-pieces of repeating units in which 2≤n≤1000; and R represents a hydrogen atom or a monovalent organic group having 1 to 30 carbon atoms.

The compounds shown by the general formula (1-2) are preferable as the compound described above.

The present invention also provides a composition for forming an organic film, comprising:

(A) a compound having two or more partial structures shown by the following general formula (1-1) in the molecule, and (B) an organic solvent,

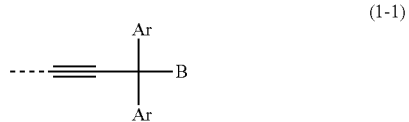
(1-1)

wherein each Ar independently represents an aromatic ring optionally having a substituent or an aromatic ring that contains at least one nitrogen atom optionally having a substituent, and two Ars are optionally bonded with each other to form a ring structure; a broken line represents a bond with an organic group; B represents an anionic leaving group that is capable of forming a reactive cation due to effect of either or both of heat and acid.

The inventive composition like this is curable under film-forming conditions in an inert gas not only in air to form an organic film that combines higher heat resistance, higher dry etching durability, and improved gap filling/planarizing characteristics.

In this case, the compound of the component (A) is preferably a compound shown by the following general formula (1-2),

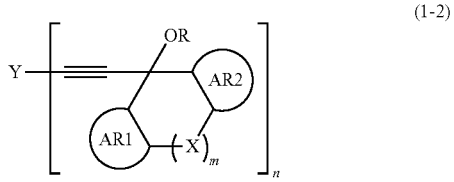
(1-2)

wherein AR1 and AR2 each represent a benzene ring, a naphthalene ring, or a pyridine ring optionally having an alkoxy group, an alkenyloxy group, or an aryloxy group having 1 to 30 carbon atoms; "m" is 0 or 1; when m=0, the aromatic rings of AR1 and AR2 do not form a bridged structure with each other, when m=1, AR1 and AR2 form a bridged structure in which the aromatic rings of AR1 and AR2 are bonded with each other through X; X represents a single bond or any of groups shown by the following formulae (3);

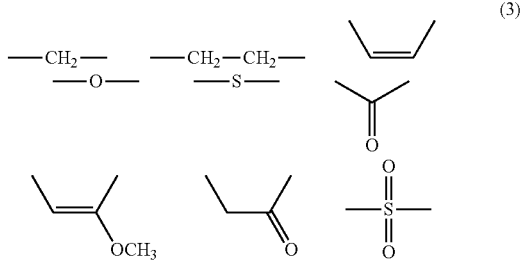
(3)

Y represents an n-valent organic group having 1 to 30 carbon atoms in which n=2 to 4 or an organic group-containing polymer having n-pieces of repeating units in which $2 \le n \le 1000$; and R represents a hydrogen atom or a monovalent organic group having 1 to 30 carbon atoms.

The compounds shown by the general formula (1-2) are preferable as the compound of the component (A).

The inventive composition for forming an organic film can further contain one or more components selected from the group consisting of (C) an acid generator, (D) a surfactant, (E) a compound having a partial structure of an aromatic ring other than the compound of the component (A), and (F) a plasticizer.

The inventive composition for forming an organic film can contain one or more components from the components (C) to (F) in accordance with the purpose.

In this case, the component (E) preferably has a weight average molecular weight of 500 to 100,000.

The component (E) like this is preferable since the film forming by baking does not cause volatilization of the component (E) from the film and can secure thermal fluidity of the material to bring particularly excellent characteristics of gap filling and planarizing a substrate.

The present invention also provides a substrate for manufacturing a semiconductor apparatus, comprising a basis substrate and an organic film formed on the basis substrate, the organic film being a cured material of the composition for forming an organic film described above.

In the inventive substrate for manufacturing a semiconductor apparatus, a highly planarized organic film is formed having higher heat resistance and higher dry etching durability. Accordingly, a semiconductor apparatus can be manufactured in high yield using the inventive substrate for manufacturing a semiconductor apparatus.

The present invention further provides a method for forming an organic film applied in a semiconductor apparatus manufacturing process, the method comprising:

applying the composition for forming an organic film described above on a body to be processed by spin coating; and heating the body to be processed, on which the composition for forming an organic film has been applied, at a temperature of 50° C. or more and 600° C. or less for 5 to 7200 seconds in an inert gas atmosphere to form a cured film.

The present invention also provides a method for forming an organic film applied in a semiconductor apparatus manufacturing process, the method comprising:

applying the composition for forming an organic film described above on a body to be processed by spin coating;

heating the body to be processed, on which the composition for forming an organic film has been applied, at a temperature of 50° C. or more and 300° C. or less for 5 to 600 seconds in air to form a coating film, and heating the body to be processed, on which the coating film has been formed, subsequently at a temperature of 200° C. or more and 600° C. or less for 10 to 7200 seconds in an inert gas atmosphere to form a cured film.

The organic film formed by the inventive method, which is applied in a process for manufacturing a semiconductor apparatus, has higher heat resistance and higher dry etching durability. Accordingly, a semiconductor apparatus can be manufactured in high yield using the inventive substrate for manufacturing a semiconductor apparatus.

In this case, the inert gas preferably has an oxygen content of 1% or less.

The inventive composition for forming an organic film is capable of forming a sufficiently cured organic film without forming a sublimate even when it is heated in such an inert gas atmosphere.

As the body to be processed, it is possible to use a body to be processed having steps or a structure with a height of 30 nm or more.

The inventive method for forming an organic film is particularly useful for forming a planar organic film on such a body to be processed.

The present invention also provides a patterning process comprising:

forming an organic film on a body to be processed from the composition for forming an organic film described above;

forming a silicon-containing resist middle layer film on the organic film from a resist middle layer film material containing silicon;

forming a resist upper layer film on the silicon-containing resist middle layer film from a resist upper layer film material composed of a photoresist composition;

forming a circuit pattern in the resist upper layer film;

transferring the pattern to the silicon-containing resist middle layer film by etching using the resist upper layer film having the formed circuit pattern as a mask;

transferring the pattern to the organic film by etching using the silicon-containing resist middle layer film having the transferred pattern as a mask; and transferring the pattern to the body to be processed by etching using the organic film having the transferred pattern as a mask.

The present invention further provides a patterning process comprising:

forming an organic film on a body to be processed from the composition for forming an organic film described above;

forming a silicon-containing resist middle layer film on the organic film from a resist middle layer film material containing silicon;

forming an organic antireflective film on the silicon-containing resist middle layer film;

forming a resist upper layer film on the organic antireflective film from a resist upper layer film material composed of a photoresist composition to form a four-layered film structure;

forming a circuit pattern in the resist upper layer film;

transferring the pattern to the organic antireflective film and the silicon-containing resist middle layer film by etching using the resist upper layer film having the formed circuit pattern as a mask;

transferring the pattern to the organic film by etching using the silicon-containing resist middle layer film having the transferred pattern as a mask; and transferring the pattern to the body to be processed by etching using the organic film having the transferred pattern as a mask.

The present invention further provides a patterning process comprising:

forming an organic film on a body to be processed from the composition for forming an organic film described above;

forming an inorganic hard mask selected from a silicon oxide film, a silicon nitride film, a silicon oxynitride film, a titanium oxide film, and a titanium nitride film on the organic film;

forming a resist upper layer film on the inorganic hard mask from a resist upper layer film material composed of a photoresist composition;

forming a circuit pattern in the resist upper layer film;

transferring the pattern to the inorganic hard mask by etching using the resist upper layer film having the formed circuit pattern as a mask;

transferring the pattern to the organic film by etching using the inorganic hard mask having the transferred pattern as a mask; and transferring the pattern to the body to be processed by etching using the organic film having the transferred pattern as a mask.

The present invention further provides a patterning process comprising:

forming an organic film on a body to be processed from the composition for forming an organic film described above;

forming an inorganic hard mask selected from a silicon oxide film, a silicon nitride film, a silicon oxynitride film, a titanium oxide film, and a titanium nitride film on the organic film;

forming an organic antireflective film on the inorganic hard mask;

forming a resist upper layer film on the organic antireflective film from a resist upper layer film material composed of a photoresist composition to form a four-layered film structure;

forming a circuit pattern in the resist upper layer film;

transferring the pattern to the organic antireflective film and the inorganic hard mask by etching using the resist upper layer film having the formed circuit pattern as a mask;

transferring the pattern to the organic film by etching using the inorganic hard mask having the transferred pattern as a mask; and transferring the pattern to the body to be processed by etching using the organic film having the transferred pattern as a mask.

The inventive composition for forming an organic film can be suitably used for various patterning processes such as a 3-layer resist process using a silicon-containing resist middle layer film or an inorganic hard mask, and a 4-layer resist process using an organic antireflective film in addition to the above. In a process for manufacturing a semiconductor apparatus, when a circuit pattern is formed by the inventive patterning processes like this, a semiconductor apparatus can be manufactured in a good yield.

In this case, the inorganic hard mask is preferably formed by a CVD method or an ALD method.

In the inventive patterning process, the inorganic hard mask can be formed by such a method, for example.

In this case, it is preferable that the circuit pattern be formed by a photolithography with a wavelength ranging from 10 nm to 300 nm, a direct drawing by electron beam, a nanoimprinting, or a combination thereof.

In forming the pattern described above, it is preferable that the circuit pattern be developed by alkaline development or development with an organic solvent.

In the inventive patterning process, these means for forming a circuit pattern and development means can be favorably used.

It is preferable that the body to be processed be a semiconductor apparatus substrate or the semiconductor apparatus substrate coated with any of a metal film, a metal carbide film, a metal oxide film, a metal nitride film, a metal oxycarbide film, and a metal oxynitride film.

It is preferable that the body to be processed contain silicon, titanium, tungsten, hafnium, zirconium, chromium, germanium, copper, silver, gold, aluminum, indium, gallium, arsenic, palladium, iron, tantalum, iridium, cobalt, manganese, molybdenum, or an alloy thereof.

The inventive patterning process makes it possible to process the body to be processed described above to form a pattern.

Advantageous Effects of Invention

As described above, the inventive compound is a compound that is curable in film forming in an inert gas, which prevents a substrate from corrosion, without forming byproducts, and is useful for forming an organic under layer film that has improved gap filling and planarizing characteristics. The composition for forming an organic film containing this compound is a material that has excellent gap filling/planarizing characteristics and is capable of forming an organic film with various properties such as heat resistance and etching durability. Accordingly, they are very useful as an organic film material in multilayer resist processes such as a two-layer resist process, a three-layer resist process using a silicon-containing middle layer film, and a four-layer resist process using a silicon-containing middle layer film and an organic antireflective film as well as a planarization material for producing a semiconductor device. The organic film formed from the inventive composition for forming an organic film is excellent in heat resistance, and do not cause fluctuation of the film thicknesses due to thermal decomposition even in forming a CVD (Chemical Vapor Deposition) hard mask on the organic under layer film. Therefore, it is favorable for patterning.

BRIEF DESCRIPTION OF DRAWINGS

FIG. 1 is an explanatory diagram of the planarizing characteristics in the present invention;
FIG. 2 is an explanatory diagrams of an example of a patterning process by the three-layer resist process in the present invention;
FIG. 3 is an explanatory diagrams of a method for evaluating the gap filing characteristics in Examples;
FIG. 4 is an explanatory diagrams of a method for evaluating the planarizing characteristics in Examples.

DESCRIPTION OF EMBODIMENTS

As described above, it has been demanded for an organic under layer film that can be formed without forming a byproduct under the film forming conditions in an inert gas, for example, at a temperature of 300° C. or more in order to prevent corrosion of a substrate, and is excellent in characteristics of gap filling and planarizing a pattern formed on a substrate as well as dry etching durability in substrate processing. Additionally, it has been demanded for an organic film that is free from fluctuating the film thickness due to decomposition in forming a CVD hard mask on the organic under layer film, together with a compound to attain these properties.

The organic under layer film is usually formed such that a compound for forming an organic film is dissolved in an organic solvent to form a composition, which is then applied onto a substrate having semiconductor device structures or wiring formed thereon and is baked. The composition forms a coating film in accordance with the shape of a step structure on the substrate immediately after application thereof. When the coating film is baked, most of the organic solvent is evaporated before curing, and an organic film is formed from the compound for forming an organic film remained on the substrate. The inventors noticed this behavior and have conceived that if the compound for forming an organic film remained on the substrate has sufficient thermal fluidity, the thermal fluidization causes planarization of the step structure immediately after the application, thereby making it possible to form a planar film.

The inventors have diligently investigated compounds each having a triple bond to find that the compound having two or more partial structures shown by the following general formula (1-1) as an intermolecular crosslinking group in the molecule, that is, the compound having partial structures containing a quadrivalent carbon that has two aromatic substituents as well as substituents of one triple bond carbon and a leaving group capable of forming a reactive cation, shows thermal curability equivalent to the previous under layer film materials even in an inert gas not only in air, does not form a byproduct to contaminate a manufacturing device of a semiconductor apparatus in the curing reaction, and gives an organic layer film that has improved gap filling/planarizing characteristics due to the good thermal fluidity, together with good dry etching durability and heat resistance such that the coating film is prevented from changing the thickness due to heat decomposition even in forming a CVD hard mask; thereby brought the present invention to completion.

Hereinafter, the present invention will be explained in detail, but the present invention is not limited thereto.

<Compound (1)>

The compound of the present invention is a compound having two or more structures shown by the following general formula (1-1) as partial structures in the molecule (hereinafter, referred to as Compound (1)),

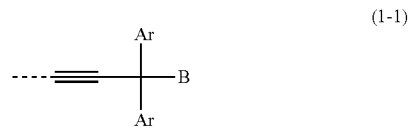

(1-1)

wherein each Ar independently represents an aromatic ring optionally having a substituent or an aromatic ring that contains at least one nitrogen atom optionally having a substituent, and two Ars are optionally bonded with each other to form a ring structure; a broken line represents a bond with an organic group; B represents an anionic leaving group that is capable of forming a reactive cation due to effect of either or both of heat and acid.

Each Ar independently represents an aromatic ring that may have a substituent or an aromatic ring containing at least one nitrogen atom that may have a substituent, and the two Ars may be bonded with each other to form a ring structure. Illustrative examples of Ar like this include a benzene ring, a naphthalene ring, a pyridine ring, and so on.

The broken line represents a bond with an organic group. The "organic group" in the present invention means a group that contains at least a carbon atom, which may additionally contains a hydrogen atom, and further a nitrogen atom, an oxygen atom, a sulfur atom, and/or a silicon atom, etc.

Although "B" is not limited to particular one so long as it is an anionic leaving group that is capable of forming a reactive cation due to effect of either or both of heat and acid, illustrative examples thereof include a hydroxy group, an alkoxy group, and so on.

The inventive compound is more specifically a compound shown by the following general formula (1-2) (hereinafter, referred to as Compound (2)),

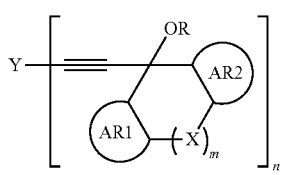
(1-2)

wherein AR1 and AR2 each represent a benzene ring, a naphthalene ring, or a pyridine ring optionally having an alkoxy group, an alkenyloxy group, or an aryloxy group having 1 to 30 carbon atoms; "m" is 0 or 1; when m=0, the aromatic rings of AR1 and AR2 do not form a bridged structure with each other, when m=1, AR1 and AR2 form a bridged structure in which the aromatic rings of AR1 and AR2 are bonded with each other through X; X represents a single bond or any of groups shown by the following formulae (3);

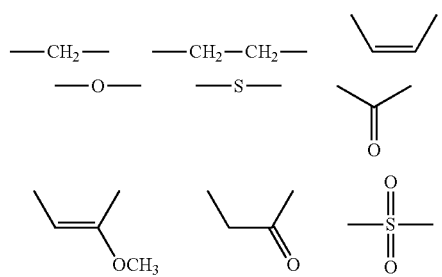
(3)

Y represents an n-valent organic group having 1 to 30 carbon atoms in which n=2 to 4 or an organic group-containing polymer having n-pieces of repeating units in which $2 \leq n \leq 1000$; and R represents a hydrogen atom or a monovalent organic group having 1 to 30 carbon atoms.

Illustrative examples of the compound (1) and (2) presented herein include the following structures, but the present invention is not limited thereto.

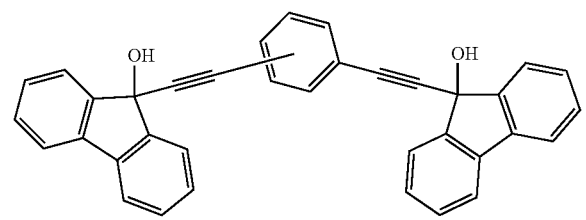

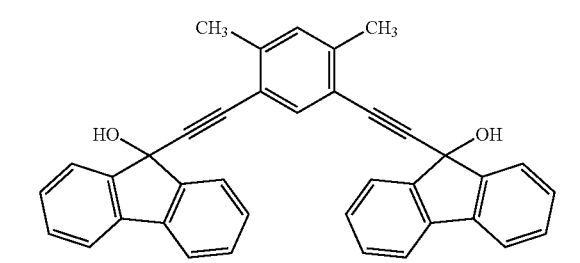

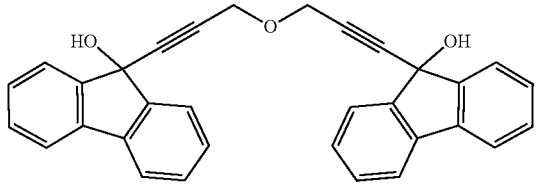

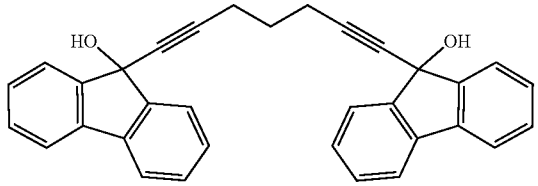

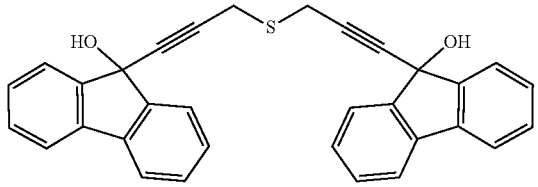

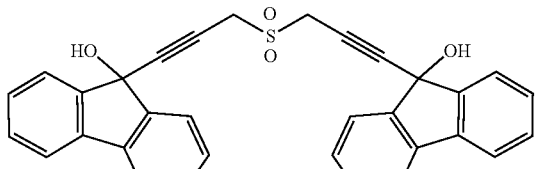

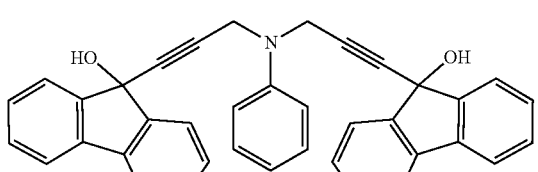

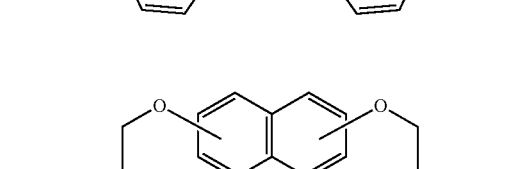

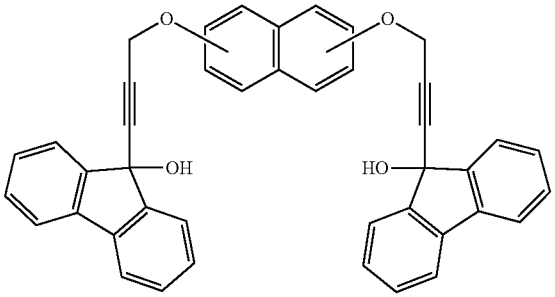

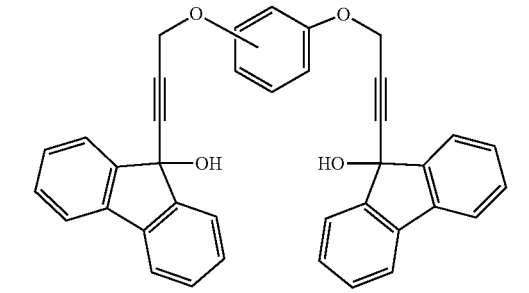

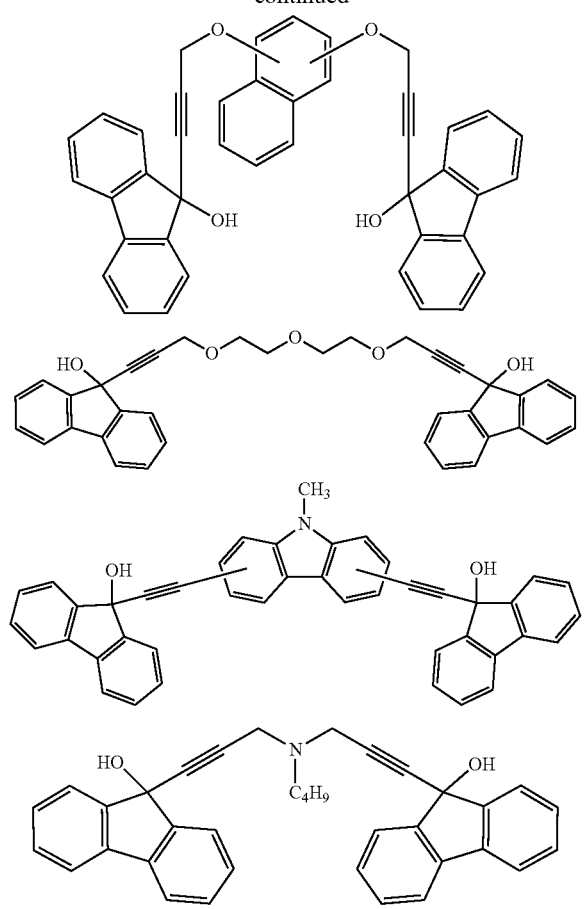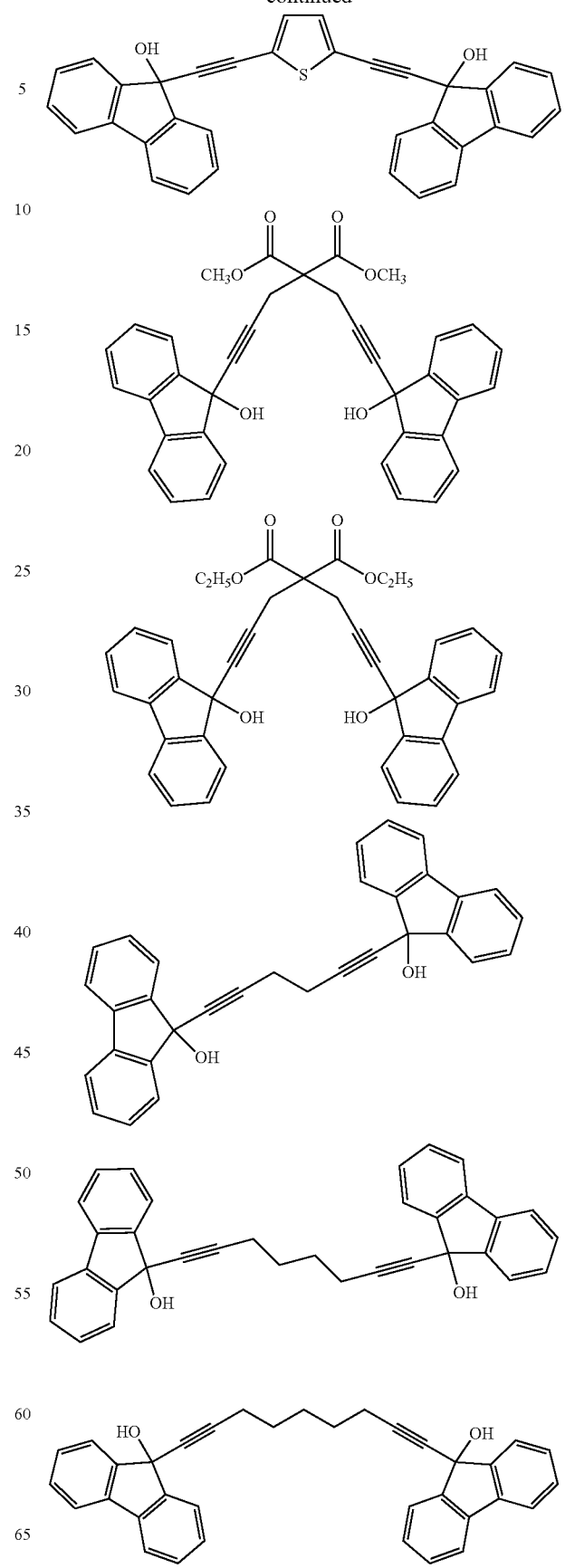

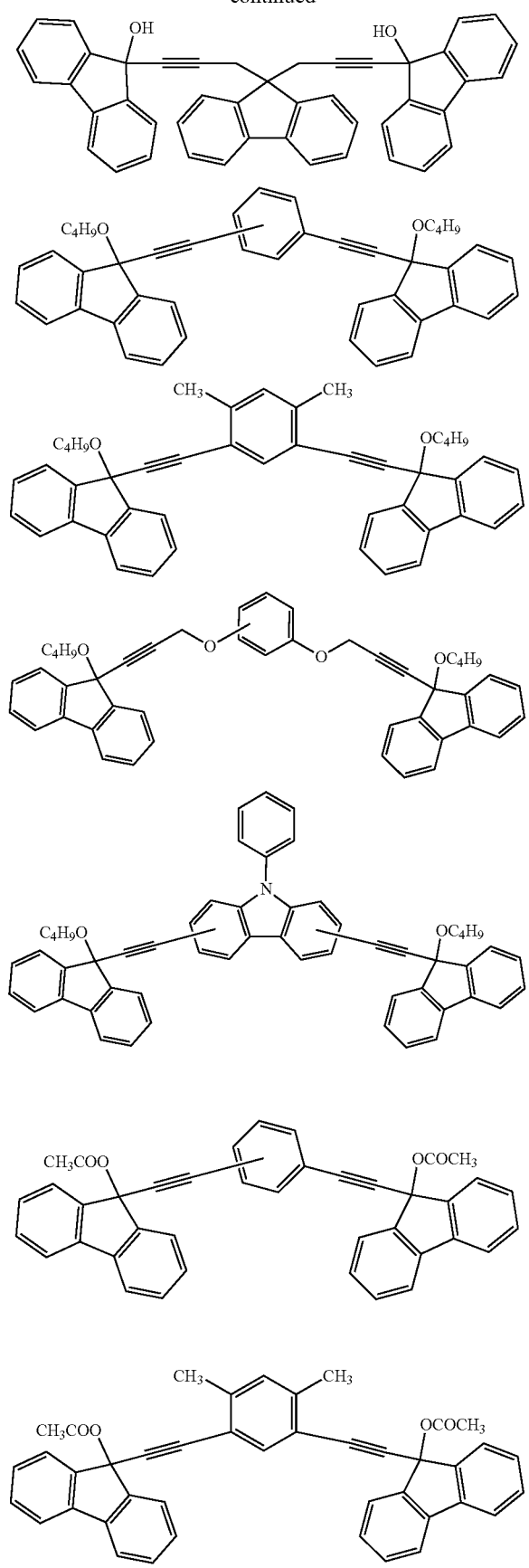
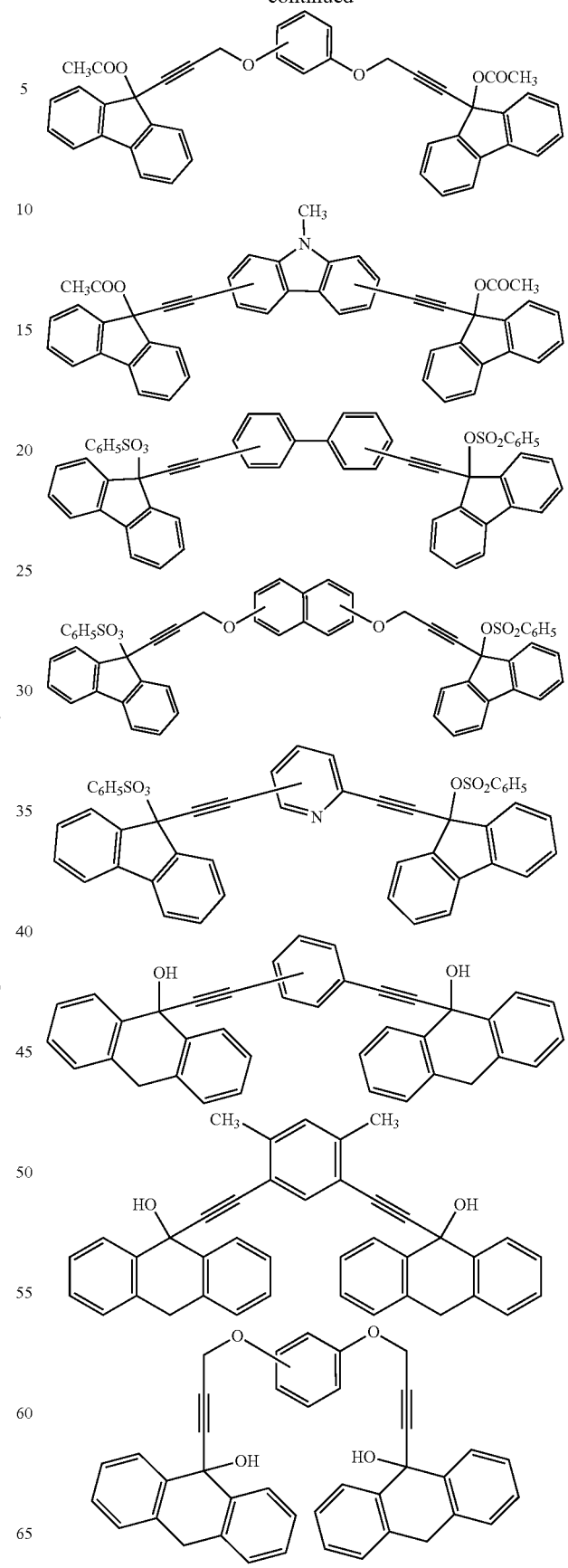

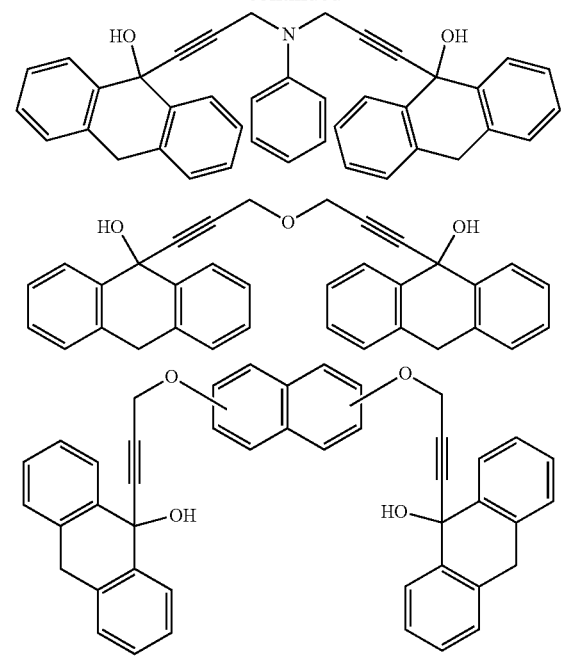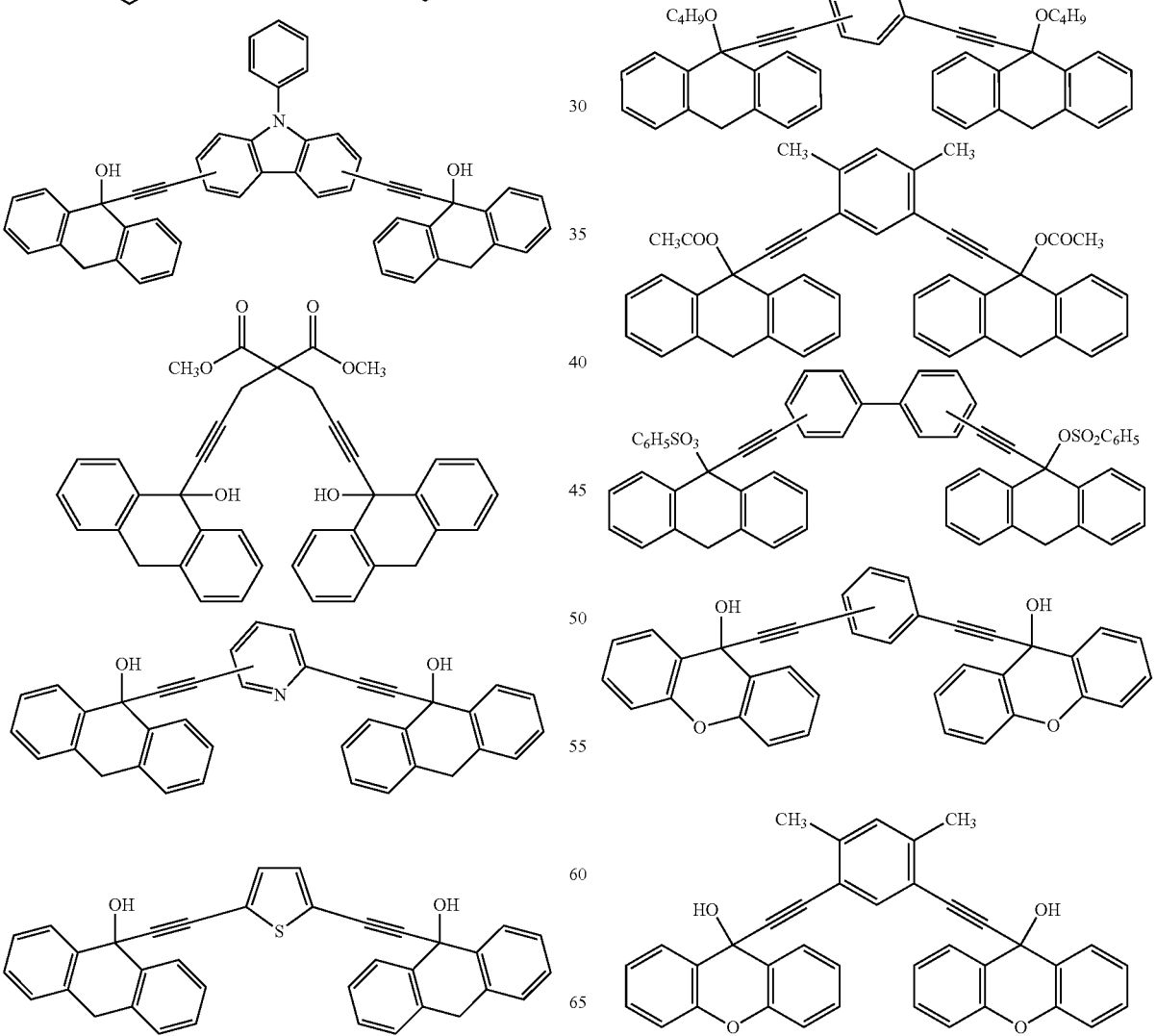

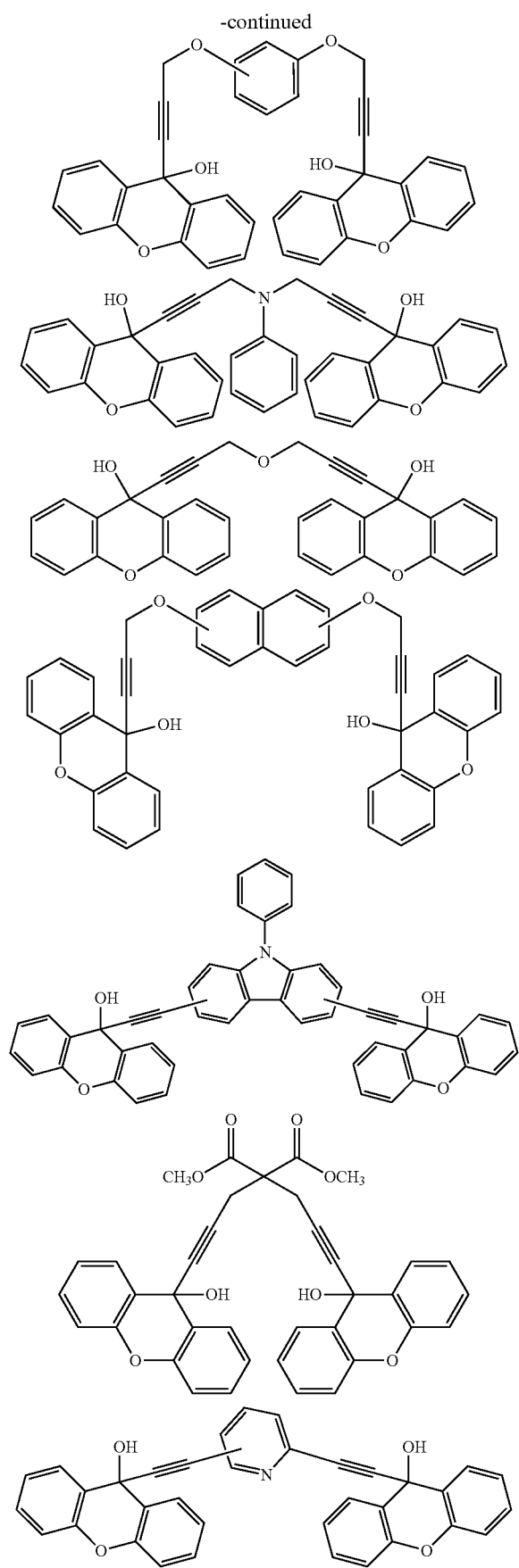

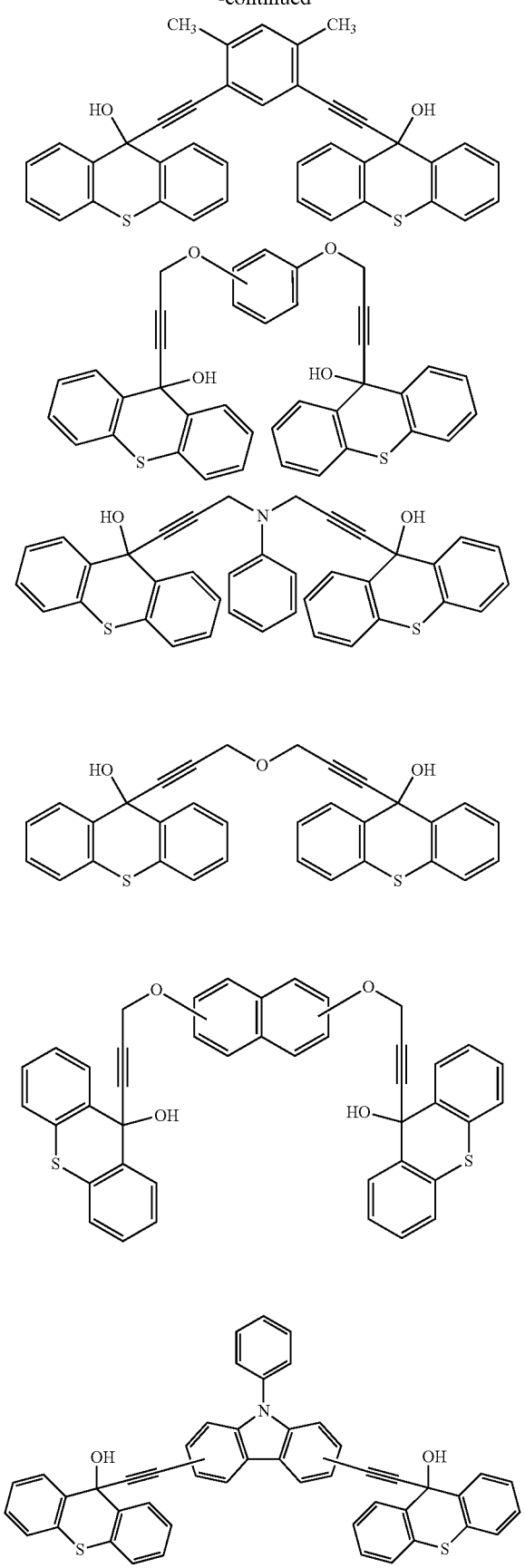

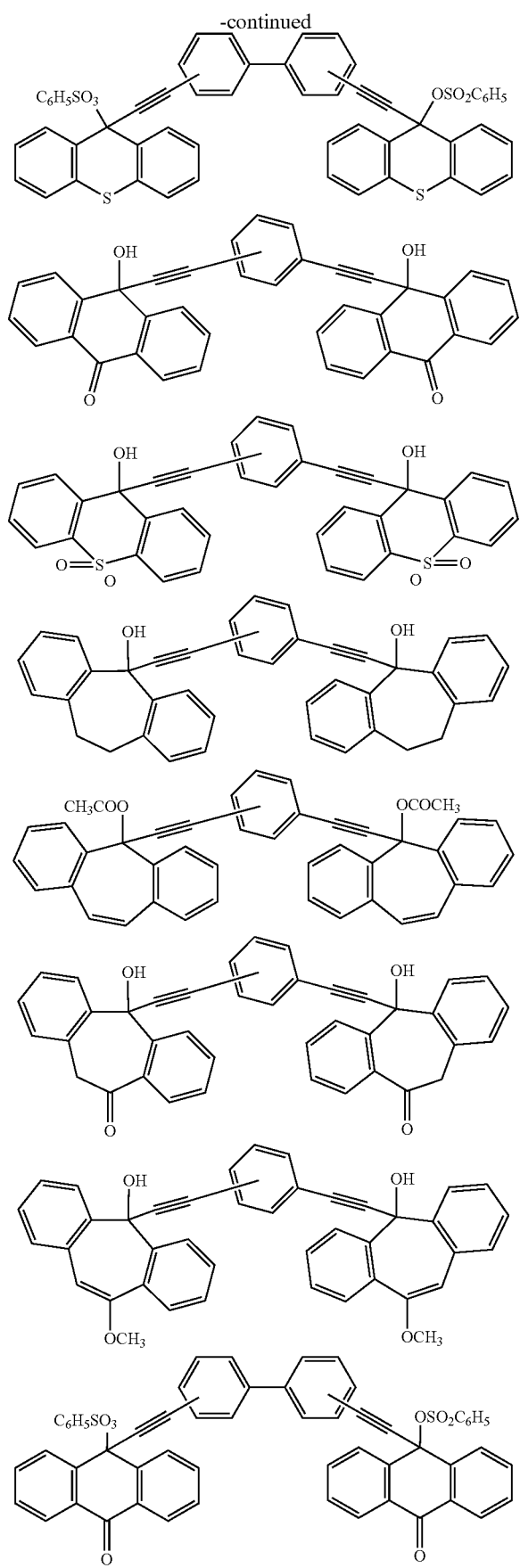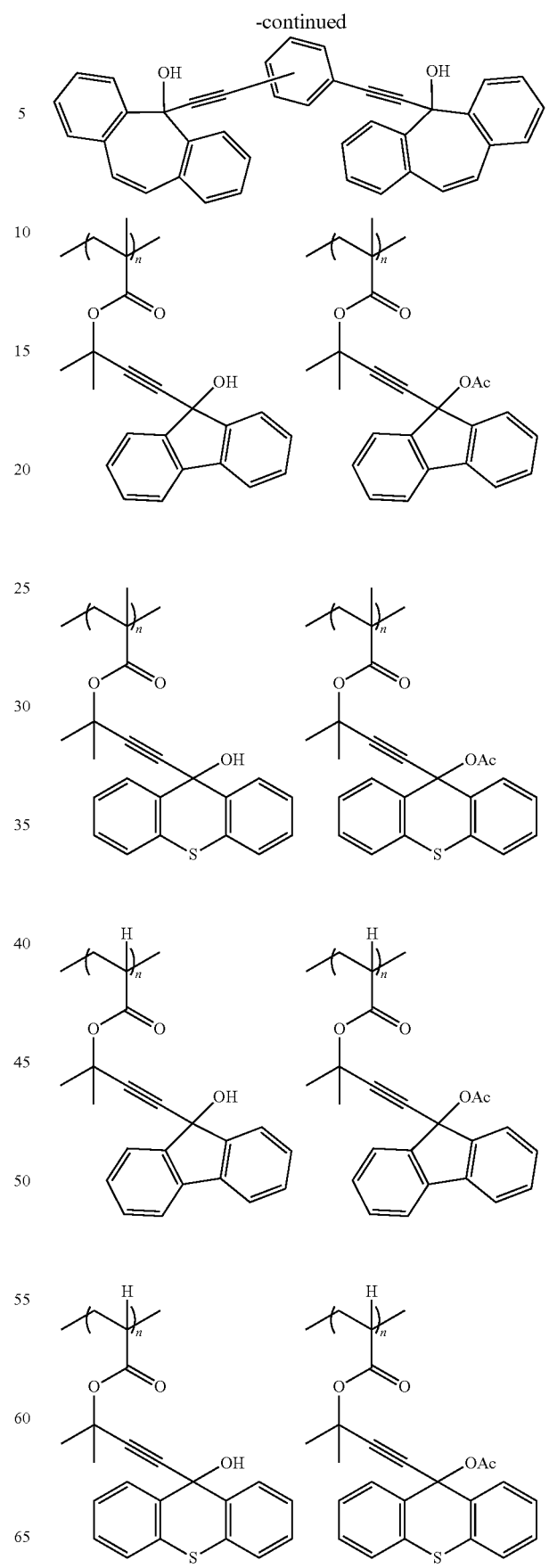

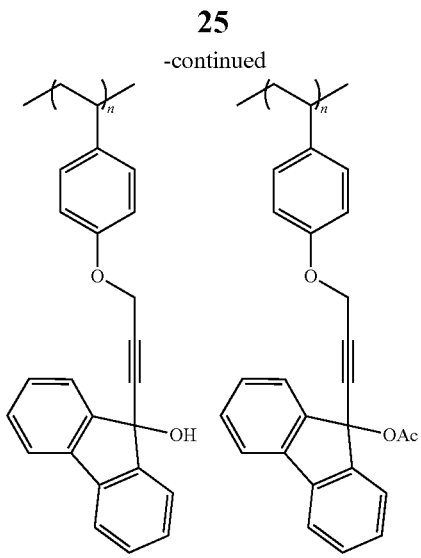

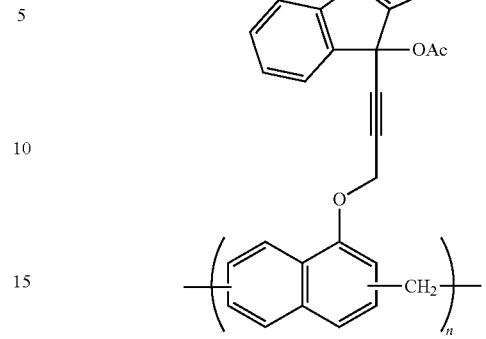

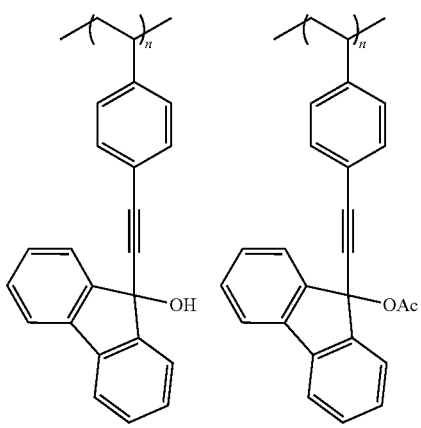

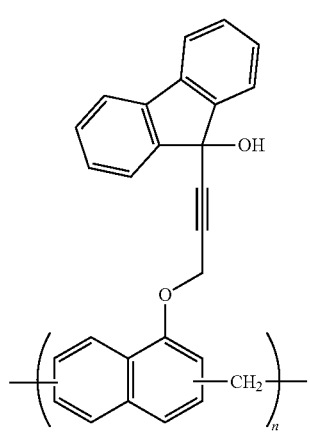

In the formulae, "n" represents the same meanings as described above.

The compound (1) and the compound (2) like these show curing properties equivalent to the previous under layer film materials even in an inert gas and give an organic film having higher heat resistance as well as improved characteristics of gap filling and planarizing a substrate.

[Method for Manufacturing Compound]

Illustrative examples of method for manufacturing the inventive compound (1) include a method in which an alcohol (iii) is obtained by addition reaction of an ethynyl compound (ii) to the ketone compound (i) (Formula 1), and the hydroxy group is protected to obtain (iv) (Formula 2) in accordance with needs.

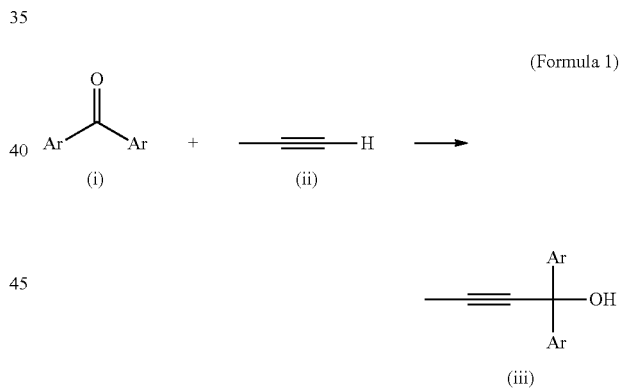

(Formula 1)

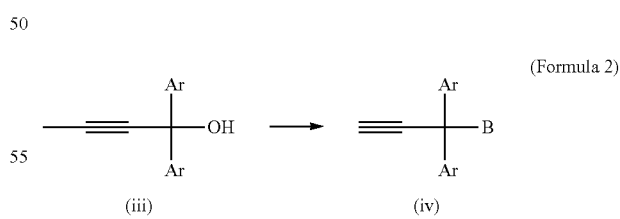

(Formula 2)

In the formulae, Ar, the broken line, and B represent the same meanings as described above.

More specifically, illustrative examples of the method for manufacturing the inventive compound (2) include a method in which an alcohol (vii) is obtained by addition reaction of an ethynyl compound (vi) to the ketone compound (v) (Formula 3), and the hydroxy group is protected to obtain (viii) (Formula 4) in accordance with needs.

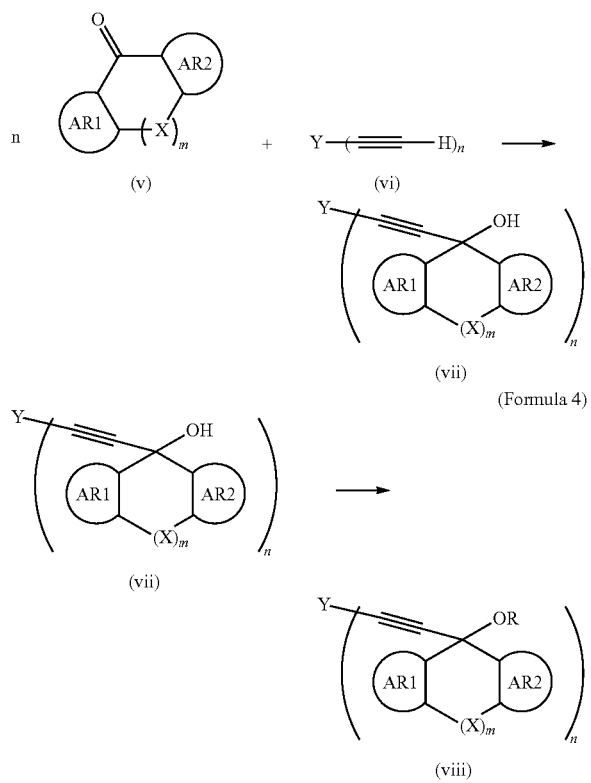

In the formulae, AR1, AR2, "m", "n", X, Y, and R represent the same meanings as described above.

In (Formula 1) and (Formula 3) described above, it is preferable to use the ethynyl compound (ii) or (vi) in an amount of 0.2/n' to 40/n' mol, particularly 0.5/n' to 2/n' mol relative to 1 mol of the ketone compound (i) or (v). Incidentally, "n'" represents a number of the partial structure shown by the general formula (1-1) contained in the compound (1) or the compound (2) and is 2 or more, particularly the same as "n" described above.

In the reaction between the ketone compound (i) or (v) and the ethynyl compound (ii) or (vi), addition reaction using a base can be exemplified. Illustrative examples of the usable base include inorganic basic compounds such as sodium hydrogencarbonate, sodium carbonate, potassium carbonate, calcium carbonate, cesium carbonate, sodium hydroxide, potassium hydroxide, sodium hydride, and potassium phosphate; alkoxides such as sodium methoxide, sodium ethoxide, and potassium t-butoxide; organic amine compounds such as triethylamine, pyridine, and N-methylmorpholine; Grignard reagents; organic lithium reagents; and metals such as Li and Na. They can be used singly or as a combination of two or more kinds. The amount of base used therein is preferably 0.2×n' to 10×n' mol, particularly 0.5×n' to 2×n' mol relative to 1 mol of the ethynyl compound (ii) or (vi).

Illustrative examples of the reaction method may include a method in which the ketone compound, the ethynyl compound, and the base are collectively introduced; a method in which the ketone compound and the ethynyl compound are dispersed or dissolved, and then the base is added collectively or dropwise subsequent to dilution with solvent; and a method in which the base is dispersed or dissolved, and then the ketone compound and the ethynyl compound are added collectively or dropwise subsequent to dilution with solvent. However, the method is preferably performed by reaction of the ethynyl compound and the base to generate an anion, followed by mixing the ketone compound thereto.

The solvent used in the reaction is not limited to particular solvents so long as it is inert to the reaction, but illustrative examples thereof include ether solvents such as diethyl ether, tetrahydrofuran, and dioxane; aromatic solvents such as benzene, toluene, and xylene; aprotic polar solvent such as acetonitrile, dimethyl sulfoxide, N,N-dimethylformamide, and N-methyl-pyrrolidone; and water. They can be used singly or as a mixture. The reaction temperature is preferably from −50° C. to about the boiling temperature of the solvent, more preferably 0° C. to 100° C. Regarding the reaction time, it is desirable to trace the reaction by chromatography and so on to complete the reaction, but it is generally recommended to perform the reaction for 30 minutes to 48 hours.

After finishing the reaction, the compound can also be collected through washing with water with a separatory funnel subsequent to dilution with an organic solvent in order to remove the unreacted raw materials, the acid catalyst, and so on remained in the system.

The organic solvent used for washing with a separatory funnel is not limited to particular solvents so long as it can dissolve the compound and separates to two layers after mixing with water, but illustrative examples thereof include hydrocarbons such as hexane, heptane, benzene, toluene, and xylene; esters such as ethyl acetate, n-butyl acetate, propylene glycol methyl ether acetate; ketones such as methyl ethyl ketone, methyl amyl ketone, cyclohexanone, and methyl isobutyl ketone; ethers such as diethyl ether, diisopropyl ether, methyl tert-butyl ether, and cyclopentyl methyl ether; chlorinated solvents such as methylene chloride, chloroform, dichloroethane, and trichloroethylene; and mixtures thereof.

Subsequently, it is possible to protect the hydroxyl group of the alcohol compound (iii) or (vii) in accordance with needs to form the compound (iv) or (viii) in order to enhance the solubility to solvent and to improve the storage stability of the compound. For example, the alcohol compound (iii) or (vii) can be derived to an ether compound by reaction with alcohol, to a carboxylic ester compound by reaction with acyl chloride or acid anhydride, or to a sulfonic ester compound by reaction with mesylic chloride or tosylic chloride. In this case, the protection reaction may be performed after the alcohol compound (iii) or (vii) is once isolated. The protection reaction may also be performed by synthesizing the alcohol compound (iii) or (vii), followed by reaction of the above reagent and the alkoxide before washing with water.

As described above, the compound of the present invention exhibits sufficient curing properties even in an inert gas and gives a composition for forming an organic film that is capable of forming an organic film with good dry etching durability and improved gap filling/planarizing characteristics combined with heat resistance against a temperature of 400° C. or more.

It is to be noted that in the present invention, the planarizing characteristics means a property to make the surface of a substrate planar. With the composition for forming an organic film that contains a compound of the present invention, it is possible to decrease a step of 100 nm in a substrate 1 to 30 nm or less by applying a composition 3' for forming an organic film onto the substrate 1, followed by heating to form an organic film 3 as shown in FIG. 1, for example. Incidentally, the stepped profile shown in FIG. 1 represents a typical example of the stepped profiles in substrates for semiconductor device production, and the stepped profile of a substrate that can be planarized by the composition for forming an organic film that contains a compound of the present invention is not limited thereto.

<Composition for Forming Organic Film>

The present invention also provides a composition for forming an organic film that contains (A) the above compound (i.e., the compound having two or more partial structures shown by the general formula (1-1) in the molecule) and (B) an organic solvent. The present invention further provides a composition for forming an organic film that additionally contains one or more of (C) an acid generator, (D) a surfactant, (E) a compound having a partial structure of an aromatic ring other than the compound of the component (A), and (F) a plasticizer.

Incidentally, in the inventive composition for forming an organic film, the inventive compound of the component (A) can be used singly or in combination of two or more kinds.

The organic solvent (B) that is usable for the inventive composition for forming an organic film is not particularly limited so long as it dissolves the above base polymer, the acid generator, the crosslinking agent, and other additives. Specifically, it is possible to use solvents having a boiling point less than 180° C. such as solvents described in paragraphs [0091]-[0092] of Japanese Patent Laid-Open Publication No. 2007-199653. Among them, propylene glycol monomethyl ether acetate, propylene glycol monomethyl ether, 2-heptanone, cyclopentanone, cyclohexanone, and a mixture of two or more kinds of these are preferably used.

The composition like this is a composition for forming an organic film that can be applied by spin coating to bring excellent dry etching durability as well as heat resistance at a temperature of 400° C. or more and improved gap filling/planarizing characteristics since the composition contains the inventive compound described above.

As the organic solvent of the inventive composition for forming an organic film, it is possible to add a high boiling point solvent having a boiling point of 180° C. or more to the solvent having a boiling point less than 180° C. (it is possible to use admixture of a solvent having a boiling point less than 180° C. and a solvent having a boiling point of 180° C. or more). As the high boiling point organic solvent, it is possible to use any solvent including hydrocarbons, alcohols, ketones, esters, ethers, chlorinated solvents, etc. so long as it can dissolve the compound of the component (A). Specific examples thereof include 1-octanol, 2-ethylhexanol, 1-nonanol, 1-decanol, 1-undecanol, ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol, glycerin, n-nonyl acetate, ethylene glycol monohexyl ether, ethylene glycol mono-2-ethylhexyl ether, ethylene glycol monophenyl ether, ethylene glycol monobenzyl ether, diethylene glycol monoethyl ether, diethylene glycol monoisopropyl ether, diethylene glycol mono-n-butyl ether, diethylene glycol monoisobutyl ether, diethylene glycol monohexyl ether, diethylene glycol monopheyl ether, diethylene glycol monobenzyl ether, diethylene glycol diethyl ether, diethylene glycol dibutyl ether, diethylene glycol butyl methyl ether, triethylene glycol dimethyl ether, triethylene glycol monomethyl ether, triethylene glycol n-butyl ether, triethylene glycol butyl methyl ether, triethylene glycol diacetate, tetraethylene glycol dimethyl ether, dipropylene glycol monomethyl ether, dipropylene glycol mono-n-propyl ether, dipropylene glycol mono-n-butyl ether, tripropylene glycol dimethyl ether, tripropylene glycol monomethyl ether, tripropylene glycol mono-n-propyl ether, tripropylene glycol mono-n-butyl ether, ethylene glycol monoethyl ether acetate, ethylene glycol monobutyl ether acetate, diethylene glycol monomethyl ether acetate, diethylene glycol monoethyl ether acetate, diethylene glycol monobutyl ether acetate, triacetin, propylene glycol diacetate, dipropylene glycol monomethyl ether acetate, dipropylene glycol methyl n-propyl ether, dipropylene glycol methyl ether acetate, 1,4-butanediol diacetate, 1,3-butylene glycol diacetate, 1,6-hexanediol diacetate, triethylene glycol diacetate, γ-butyrolactone, dihexyl malonate, diethyl succinate, dipropyl succinate, dibutyl succinate, dihexyl succinate, dimethyl adipate, diethyl adipate, and dibutyl adipate, which can be used singly or by mixture of two or more kinds.

The high boiling point solvent may be appropriately selected such that the boiling point is adjusted to a temperature of heat treatment of the composition for forming an organic film. The high boiling point solvent to be added preferably has a boiling point of 180 to 300° C., more preferably 200 to 300° C. With such a boiling point, sufficient thermal fluidity can be obtained since the baking (heat treatment) can be performed without a risk that the solvent evaporates instantly due to the boiling point being too low. With such a boiling point, the film after baking does not contain the remained solvent that has failed to evaporate, and the film properties such as etching durability are not affected.

When the high boiling point solvent is used, the blending amount of the high boiling point solvent is preferably 1 to 30 parts by mass relative to 100 parts by mass of the solvent having a boiling point less than 180° C. Such a blending amount does not cause risks that sufficient thermal fluidity cannot be obtained in baking due to too small blending amount, or the solvent remains in the film to degrade the film properties such as etching durability due to too large blending amount.

The composition for forming an organic film like this, with the compound for forming an organic film being additionally provided with thermal fluidity by adding the high boiling point solvent, securely becomes a composition for forming an organic film having improved gap filling/planarizing characteristics.

Into the inventive composition for forming an organic film, (C) acid generator can be added to promote the curing reaction further. As the acid generator, any type can be added including acid generators that generate acid by heat decomposition and acid generators that generate acid by light irradiation. Specific examples of the acid generator that can be added include materials described in paragraphs [0061]-[0085] of JP 2007-199653A, but are not limited thereto.

The above acid generator can be used singly or by mixture of two or more kinds. When the acid generator is added, the blending amount is preferably 0.05 to 50 parts by mass, more preferably 0.1 to 10 parts by mass relative to 100 parts by mass of the compound (A).

Into the inventive composition for forming an organic film, (D) a surfactant can be added to improve coatability in spin coating. The surfactant can be used includes those described in paragraphs [0142]-[0147] of JP 2009-269953A.

Into the inventive composition for forming an organic film, it is also possible to add (E) a compound having an aromatic ring as the partial structure, which is other than the compound of the component (A). As the composition for forming an organic under layer film, it is possible to use known monomer compounds and polymer compounds that contain an aromatic ring, such as known condensation resins and radically polymerizate. Illustrative examples of this component (E) include compounds containing the following repeating units and the following compounds, but not limited thereto.
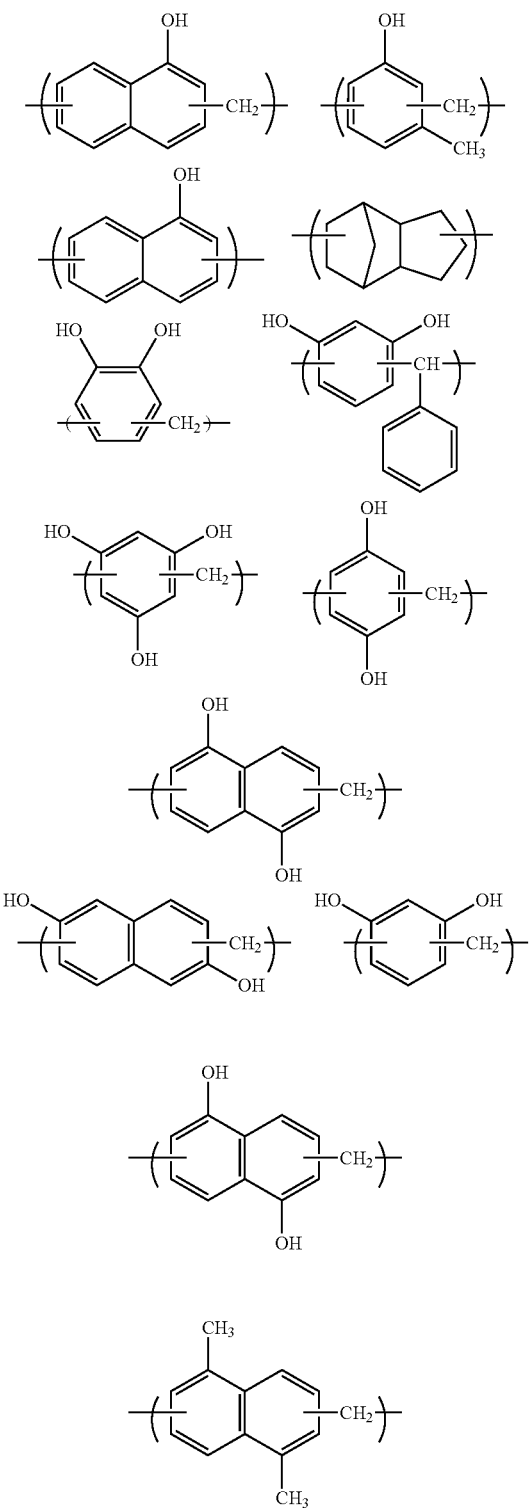
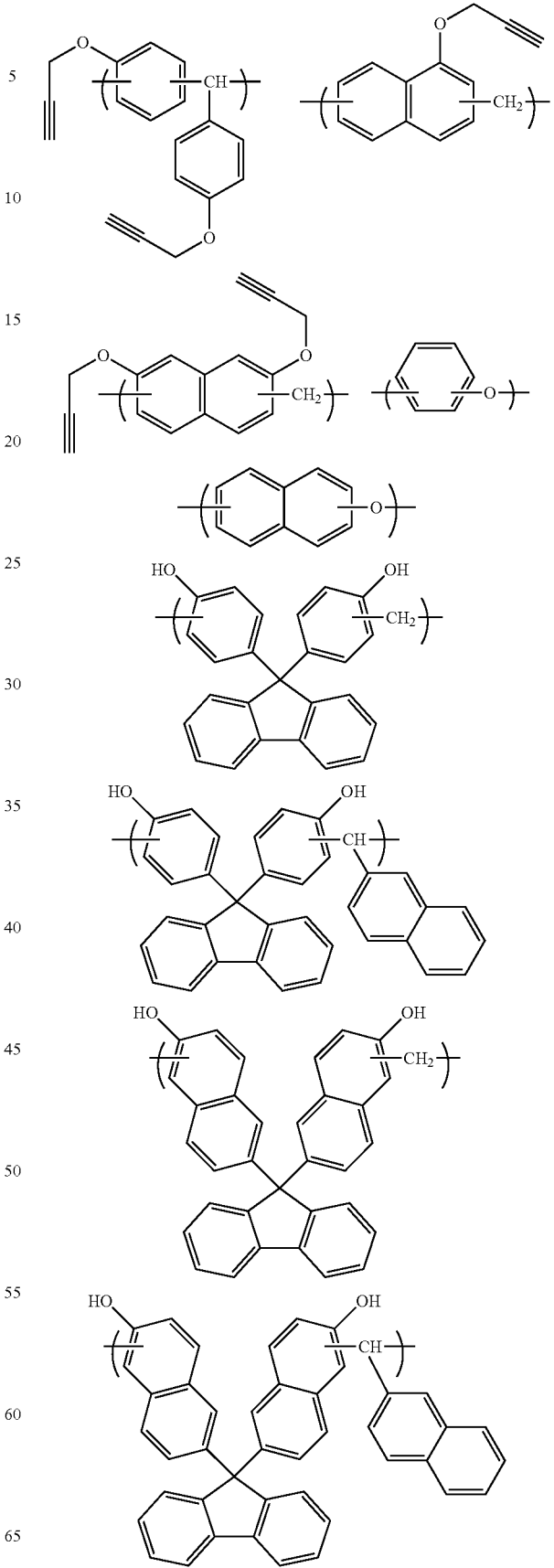

33
-continued
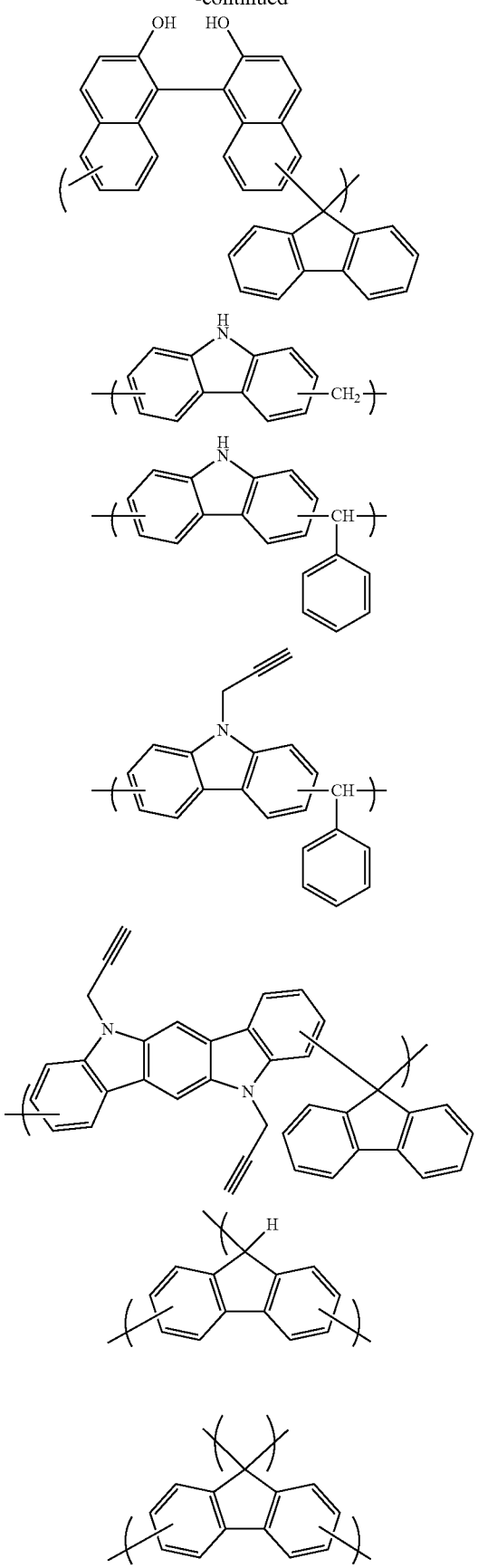
34
-continued
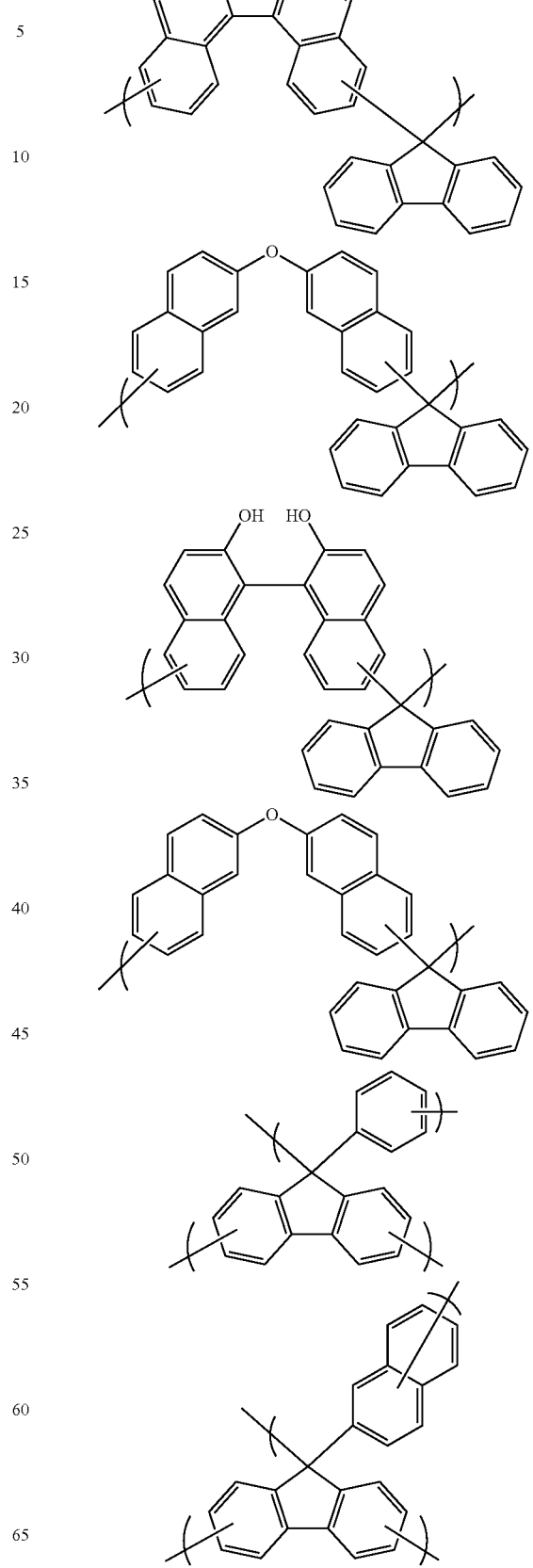

-continued

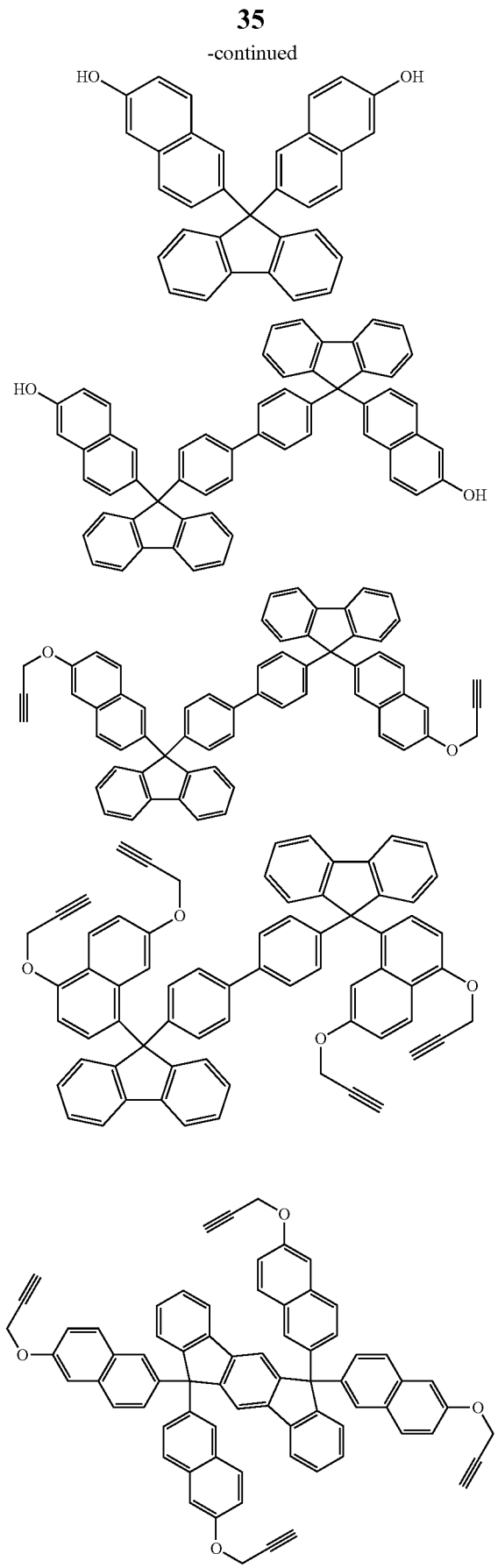

-continued

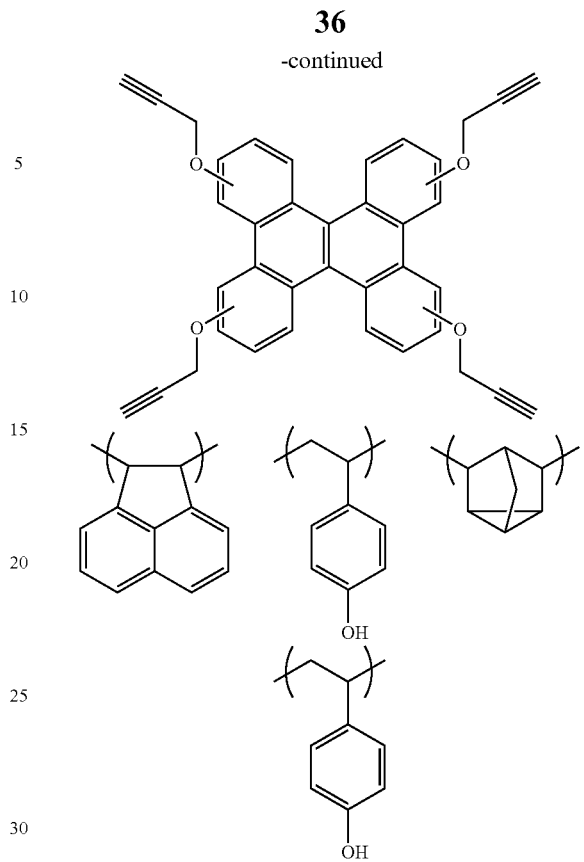

The component (E) preferably has a weight average molecular weight of 500 to 100,000, more preferably 600 to 50,000. In this range, the component (E) does not volatilize out of the film during film forming by baking, and the material can keep the thermal fluidity, making it possible to obtain sufficiently higher characteristics of gap filling and planarizing a substrate, which is preferable.

Into the inventive composition for forming an organic film, a crosslinking agent can be added to improve the curability and to further prevent intermixing with the upper layer film. The crosslinking agent is not particularly limited, and it is possible to use wide variety of known crosslinking agents in various types. Illustrative examples thereof include melamine crosslinking agents, glycoluril crosslinking agents, benzoguanamine crosslinking agents, urea crosslinking agents, β-hydroxyalkylamide crosslinking agents, isocyanurate crosslinking agents, aziridine crosslinking agents, oxazoline crosslinking agents, and epoxy crosslinking agents.

Illustrative examples of the melamine crosslinking agent include hexamethoxymethylated melamine, hexabutoxymethylated melamine, alkoxy and/or hydroxy substitutes thereof, and partial self-condensates thereof. Illustrative examples of the glycoluril crosslinking agent include tetramethoxymethylated glycoluril, tetrabutoxymethylated glycoluril, alkoxy and/or hydroxy substitutes thereof, and partial self-condensates thereof. Illustrative examples of the benzoguanamine crosslinking agent include tetramethoxymethylated benzoguanamine, tetrabutoxymethylated benzoguanamine, alkoxy and/or hydroxy substitutes thereof, and partial self-condensates thereof. Illustrative examples of the urea crosslinking agent include dimethoxymethylated dimethoxyethyleneurea, alkoxy and/or hydroxy substitutes thereof, and partial self-condensates thereof. Illustrative examples of the β-hydroxyalkylamide crosslinking agent include N,N,N',N'-tetra(2-hydroxyethyl)adipate amide. Illustrative examples of the isocyanurate crosslinking agent include triglycidylisocyanurate and triallylisocyanurate. Illustrative examples of the aziridine crosslinking agent include 4,4'-bis(ethyleneiminocarbonylamino)diphenylmethane and 2,2-bishydroxymethylbutanol-tris[3-(1-aziridinyl)propionate]. Illustrative examples of the oxazoline crosslinking agent include 2,2'-isopropylidene-bis(4-benzyl-2-oxazoline), 2,2'-isopropylidene-bis(4-phenyl-2-oxazoline), 2,2'-methylene-bis(4,5-diphenyl-2-oxazoline), 2,2'-methylene-bis(4-phenyl-2-oxazoline), 2,2'-methylene-bis(4-tert-butyl-2-oxazoline), 2,2'-bis(2-oxazoline), 1,3-phenylene-bis(2-oxazoline), 1,4-phenylene-bis(2-oxazoline), and copolymers of 2-isopropenyloxazoline. Illustrative examples of the epoxy crosslinking agent include diglycidyl ether, ethylene glycol diglycidyl ether, 1,4-butanediol diglycidyl ether, 1,4-cyclohexanedimethanol diglycidyl ether, poly(glycidyl methacrylate), trimethylolethane triglycidyl ether, trimethylolpropane triglycidyl ether, and pentaerythritol tetraglycidyl ether.

Into the inventive composition for forming an organic film, (F) a plasticizer can be added to further improve the gap filling/planarizing characteristics. The plasticizer is not particularly limited, and it is possible to use wide variety of known plasticizers in various types. Illustrative examples thereof include low molecular weight compounds such as phthalate esters, adipate esters, phosphate esters, trimellitate esters, and citrate esters; polymers such as polyethers, polyesters, and polyacetal polymers described in JP 2013-253227A.

As an additive to bring the inventive composition for forming an organic film to have gap filling/planarizing characteristics that is same as in the case of plasticizer, the following examples are preferably used: a liquid state additive having a polyethylene glycol or polypropylene glycol structure, or heat decomposable polymer having a weight loss ratio between 30° C. and 250° C. of 40% by mass or more and a weight average molecular weight of 300 to 200,000. This heat decomposable polymer preferably contains a repeating unit having an acetal structure shown by the following general formula (DP1) or (DP1a).

(DP1)

In the formula, $R_6$ represents a hydrogen atom or a saturated or unsaturated monovalent organic group having 1 to 30 carbon atoms which may be substituted; and $Y_1$ represents a saturated or unsaturated divalent organic group having 2 to 30 carbon atoms.

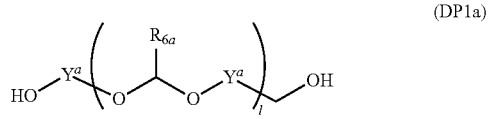
(DP1a)

In the formula, $R_{6a}$ represents an alkyl group having 1 to 4 carbon atoms; $Y^a$ represents a saturated or unsaturated divalent hydrocarbon group having 4 to 10 carbon atoms, which may have an ether bond; and "1" represents an average repeating unit number and is 3 to 500.

As described above, the inventive composition for forming an organic film forms an organic film that has excellent dry etching durability as well as heat resistance at a temperature of 400° C. or more and improved gap filling/planarizing characteristics. Accordingly, it is very useful for an organic under layer film material used for multilayer resist processes such as a two-layer resist process, a three-layer resist process using a silicon-containing resist middle layer film or a silicon-containing inorganic hard mask, and a four-layer resist process using a silicon-containing resist middle layer film or a silicon-containing inorganic hard mask and an organic antireflective film. The inventive composition for forming an organic film has excellent gap filling/planarizing characteristics without forming byproducts even in film forming in an inert gas, and is favorably used as a planarization material in a production step of a semiconductor device other than the multilayer resist processes.

<Method for Forming Organic Film>

The heating step of film forming for forming an organic film can employ one-stage baking, two-stage baking, or multi-stage baking with three or more stages, but one-stage baking or two-stage baking is economical and preferable. The film forming by one-stage baking is preferably performed at a temperature of 50° C. or more and 600° C. or less for 5 to 7200 seconds, particularly at a temperature of 150° C. or more and 500° C. or less for 10 to 3600 seconds. The inventive composition for forming an organic film can be cured by heating not only in air but also in an inert gas atmosphere. The heat treatment under these conditions makes it possible to promote the planarization by thermal fluidity and the crosslinking reaction.

That is, the present invention provides a method for forming an organic film applied in a semiconductor apparatus manufacturing process, the method involving applying the composition for forming an organic film described above by spin coating; heating a body to be processed having the composition for forming an organic film applied thereto, with the heating conditions being set at a temperature of 50° C. or more and 600° C. or less for 5 to 7200 seconds in an inert gas atmosphere to form a cured film.

In multilayer resist processes, a coating-type silicon middle layer film or a CVD hard mask is optionally formed onto that obtained film. When the coating-type silicon middle layer film is applied, the organic under layer film is preferably formed at a temperature higher than the temperature to form the silicon middle layer film. The silicon middle layer film is usually formed at a temperature of 100° C. or more and 400° C. or less, preferably 150° C. or more and 350° C. or less. When the organic under layer film is formed at a temperature higher than this temperature, it is possible to prevent the organic under layer film from being dissolved by a composition for forming the silicon middle layer film to form an organic film without mixing with the composition. Additionally, it is possible to eliminate the risk that the organic under layer film causes heat decomposition to form byproducts during forming the silicon middle layer film.

When the CVD hard mask is applied, the organic under layer film is preferably formed at a temperature higher than the temperature to form the CVD hard mask. As the temperature to form the CVD hard mask, a temperature of 150° C. or more and 500° C. or less can be exemplified.

On the other hand, in film forming by two-stage baking, when the first-stage baking is performed in air atmosphere, this baking is performed under the conditions that the upper limit of the treatment temperature in air atmosphere is set to 300° C. or less, preferably 250° C. or less and in a range of 5 to 600 seconds if the substrate can cause corrosion due to oxygen. The second-stage in an inert gas is preferably performed by setting the baking temperature to a temperature higher than the baking temperature in the first-stage and 600° C. or less, preferably 500° C. or less for 10 to 7200 seconds. In multilayer resist processes, a coating-type silicon middle layer film or a CVD hard mask is optionally formed onto that obtained film. When the coating-type silicon middle layer film is applied, the organic under layer film is preferably formed at a temperature higher than the temperature to form the silicon middle layer film. The silicon middle layer film is usually formed at a temperature of 100° C. or more and 400° C. or less, preferably 150° C. or more and 350° C. or less. When the organic under layer film is formed at a temperature higher than this temperature, it is possible to prevent the organic under layer film from being dissolved by a composition for forming the silicon middle layer film to form an organic film without mixing with the composition. Additionally, it is possible to eliminate the risk that the organic under layer film causes heat decomposition to form byproducts during forming the silicon middle layer film.

When the CVD hard mask is applied in the two-stage baking, the organic under layer film is preferably formed at a temperature higher than the temperature to form the CVD hard mask. As the temperature to form the CVD hard mask, a temperature of 150° C. or more and 500° C. or less can be exemplified.

The present invention also provides a method for forming an organic film, which functions as an organic under layer film used for a semiconductor apparatus manufacturing process, in which a cured film is formed by heat treatment of a substrate to be processed in an inert gas atmosphere having an oxygen content of 1% or less in order to prevent corrosion of the substrate to be processed.

In this method for forming an organic film, the inventive composition for forming an organic film described above is spin coated onto a substrate to be processed in the first place. After the spin coating, in two-stage baking, the first baking step is performed in air at a temperature of 300° C. or less, and then the second-stage baking step is performed in an atmosphere with the oxygen concentration of 1% or less. In case of one stage baking, the first-stage baking in air can be skipped. Incidentally, illustrative examples of the atmosphere in baking include inert gases such as nitrogen, argon, and helium. The inventive material is capable of forming a sufficiently cured organic film without forming sublimated products even when it is heated in such an inert gas atmosphere.

The inventive method for forming an organic film can be used for a substrate to be processed that has a structure or step with the height of 30 nm or more. As described above, the inventive composition for forming an organic film excels in gap filling/planarizing characteristics, thereby being capable of forming a planar cured film even when the substrate to be processed has a structure or a step (unevenness) with the height of 30 nm or more. That is, the inventive method for forming an organic film is particularly useful for forming a planar organic film onto such a substrate to be processed.

The thickness of an organic film to be formed is appropriately selected, but is preferably set to 30 to 20,000 nm, particularly 50 to 15,000 nm.

The above method for forming an organic film is applicable to both cases of using the inventive composition for forming an organic film that becomes an under layer film of a multilayer resist process and for forming an organic film for a planarization film.

The inventive composition for forming an organic film is usable for forming an organic film that is capable of planarizing the surface of a stepped substrate used in a production process of a semiconductor device, and is applicable to a method for forming an organic film in which the inventive composition for forming an organic film is spin coated onto a substrate to be processed, the substrate coated with the composition for forming an organic film is subjected to heat treatment in air atmosphere at a temperature of 50° C. or more and 300° C. or less for 5 to 600 seconds, and subsequently subjected to heat treatment in an inert gas at a temperature of 200° C. or more and 600° C. or less for 10 to 7200 seconds to form a cured film.

In the first step of the method for forming an organic film, the inventive composition for forming an organic film described above is spin coated onto a substrate to be processed. The use of a spin coating method allows to securely obtain good gap filling characteristics. After the spin coating, baking (heat treatment) is performed in order to promote the planarization by thermal fluidization and subsequent crosslinking reaction. It is to be noted that this baking allows the solvent in the composition to evaporate, and is capable of preventing mixing even when a resist upper layer film or a silicon-containing resist middle layer film is formed on the organic film.

<Patterning Process>

[Three-Layer Resist Process Using Silicon-Containing Resist Middle Layer Film]

In the present invention, the patterning process can be performed such that an organic film is formed on a body to be processed by using the inventive composition for forming an organic film, a silicon-containing resist middle layer film is formed on the organic film by using a silicon atom-containing film-forming material, a resist upper layer film is formed on the silicon-containing film by using a resist upper layer film material composed of a photoresist composition, a circuit pattern is formed in the resist upper layer film, the pattern is transferred to the silicon-containing resist middle layer film by etching using the patterned resist upper layer film as a mask, the pattern is transferred to the organic film by etching using the patterned silicon-containing resist middle layer film as a mask, and the pattern is transferred to the body to be processed by etching using the patterned organic film as a mask.

As the substrate to be processed, it is preferable to use a semiconductor device substrate or the semiconductor device substrate having any of a film selected from a metal film, a metal carbide film, a metal oxide film, a metal nitride film, a metal oxycabide film, and a metal oxynitride film formed thereon. Although it is not particularly limited, specific examples thereof include substrates of Si, α-Si, p-Si, $SiO_2$, SiN, SiON, W, TiN, and Al, for example, and these substrate having the above metal film and so on formed thereon as a layer to be processed.

As the layer to be processed, various Low-k films and their stopper films can be used, including Si, $SiO_2$, SiON, SiN, p-Si, α-Si, W, W—Si, Al, Cu, and Al—Si, which can be formed to a thickness of 50 to 10,000 nm usually, and particularly 100 to 5,000 nm. It is to be noted that when a layer to be processed is formed, the substrate and the layer to be processed are made from using different materials.

Incidentally, the metal to compose the layer to be processed is preferably silicon, titanium, tungsten, hafnium, zirconium, chromium, germanium, copper, silver, gold, aluminum, indium, gallium, arsenic, palladium, iron, tantalum, iridium, cobalt, manganese, molybdenum, or alloy thereof.

As the substrate to be processed, a substrate to be processed that has a structure or a step with the height of 30 nm or more is preferably used.

When the substrate to be processed is subjected to forming of an organic film by using the inventive composition for forming an organic film, the above method for forming an organic film may be applied.

Subsequently, onto the organic film, a resist middle layer film (silicon-containing resist middle layer film) is formed by using a resist middle layer film material containing a silicon atom. This silicon-containing middle layer film material is preferably based on polysiloxane. The silicon-containing resist middle layer film can possess an antireflective effect to decrease reflection. Particularly for exposure at 193 nm, k value becomes higher to increase the reflection of a substrate when a highly aromatic-containing material with high etching selectivity from a substrate is used as the composition for forming an organic film. However, the reflection can be reduced if the silicon-containing resist middle layer film has absorption so as to have an appropriate k value. Therefore, the reflection of a substrate can be decreased to 0.5% or lower. As the silicon-containing resist middle layer film having an antireflective effect, it is preferable to use polysiloxane capable of crosslinking by acid or heat having anthracene for exposure to light of 248 nm or 157 nm, and a phenyl group or a light absorbing group containing a silicon-silicon bond for exposure to light of 193 nm in the pendant structure or polysiloxane structure.

Then, onto the silicon-containing resist middle layer film, a resist upper layer film is formed by using a resist upper layer film material composed of a photoresist composition. The resist upper layer film material may be either positive tone or negative tone, and photoresist compositions in common use can be used. The resist upper layer film material is preferably subjected to spin coating, followed by pre-baking at a temperature of 60 to 180° C. for 10 to 300 seconds. Subsequently, this is subjected to exposure, post-exposure baking (PEB), and development in accordance with a conventional method to give a resist upper layer film pattern. Incidentally, the film thickness of the resist upper layer film is not particularly limited, but is preferably 30 to 500 nm, particularly 50 to 400 nm.

Subsequently, in the resist upper layer film, a circuit pattern (resist upper layer film pattern) is formed. The circuit pattern is preferably formed by lithography using a light having a wavelength of 10 nm or more and 300 nm or less, direct drawing with an electron beam, nanoimprinting, or a combination thereof.

The light for exposure can be a high-energy beam having a wavelength of 300 nm or less, and specific examples thereof include deep ultraviolet rays, KrF excimer laser (248 nm), ArF excimer laser (193 nm), $F_2$ laser (157 nm), $Kr_2$ laser (146 nm), $Ar_2$ laser (126 nm), soft X-rays (EUV) of 3 to 20 nm, electron beams (EB), ion beams, and X-rays.

In forming the circuit pattern, the circuit pattern is preferably developed by aqueous alkaline development or organic solvent development.

Then, the pattern is transferred to the silicon-containing resist middle layer film by etching using the circuit-patterned resist upper layer film as a mask. The etching of the silicon-containing resist middle layer film, which is performed by using the resist upper layer film pattern as a mask, is preferably performed by using a fluorocarbon base gas. In this way, a silicon-containing resist middle layer film pattern is formed.

Next, the pattern is transferred to the organic film by etching using the patterned silicon-containing resist middle layer film as a mask. The etching of the organic film, in which the silicon-containing resist middle layer film pattern is used as a mask, is preferably performed by using an etching gas mainly composed of oxygen gas or hydrogen gas since silicon-containing resist middle layer films have higher etching durability against oxygen gas or hydrogen gas compared to organic materials. In this way, the organic film pattern is successfully formed.

Subsequently, the pattern is transferred to the substrate to be processed by etching using the patterned organic film as a mask. The subsequent etching of a substrate to be processed (layer to be processed) can be performed by a common method such as etching mainly with fluorocarbon base gas when the substrate to be processed is a low dielectric constant insulation film of $SiO_2$, SiN, or silica, and etching mainly with chlorine-base or bromine-base gas when the substrate to be processed is p-Si, Al, or W. When the substrate is processed by etching with fluorocarbon base gas, the silicon-containing resist middle layer film pattern is delaminated at the time of substrate processing. On the other hand, when the substrate is processed by etching with chlorine-base or bromine-base gas, the substrate processing has to be followed by dry etching delamination with fluorocarbon base gas separately performed in order to delaminate the silicon-containing resist middle layer film pattern.

The organic film obtained by using the inventive composition for forming an organic film is excellent in etching durability in the etching of a substrate to be processed as described above.

[Four-Layer Resist Process Using Silicon-Containing Resist Middle Layer Film and Organic Antireflective Film]

The present invention also provides a patterning process in which an organic film is formed on a body to be processed by using the inventive composition for forming an organic film, a silicon-containing resist middle layer film is formed on the organic film by using a silicon atom-containing resist middle layer film material, an organic antireflective film is formed on the silicon-containing resist middle layer film, a resist upper layer film is formed on the organic antireflective film by using a resist upper layer film material compound of a photoresist composition, a circuit pattern is formed on the resist upper layer film, the pattern is transferred to the organic antireflective film and the silicon-containing resist middle layer film by dry etching using the circuit-patterned resist upper layer film as a mask, the pattern is transferred to the organic film by etching using the patterned silicon-containing resist middle layer film as a mask, and the pattern is transferred to the body to be processed by etching using the patterned organic film as a mask.

Incidentally, this method can be performed in the same way as in the three layer resist process by using the silicon-containing resist middle layer film except that the organic antireflective film (bottom antireflective coating: BARC) is formed between the silicon-containing resist middle layer film and the resist upper layer film.

The organic antireflective film can be formed by spin coating using a conventional organic antireflective film material.

[Three-Layer Resist Process Using Inorganic Hard Mask]

As the patterning process by the three layer resist process using the composition for forming an organic film, the present invention also provides a patterning process in which an organic film is formed on a body to be processed by using the inventive composition for forming an organic film; an inorganic hard mask selected from a silicon oxide film, a silicon nitride film, a silicon oxynitride film, titanium oxide film, and titanium nitride film is formed on the organic film; a resist upper layer film is formed on the inorganic hard mask by using a resist upper layer film material composed of a photoresist composition; a circuit pattern is formed in the resist upper layer film; the pattern is transferred to the inorganic hard mask by etching using the circuit-patterned resist upper layer film as a mask; the pattern is transferred to the organic film by etching using the patterned inorganic hard mask as a mask; and the pattern is transferred to the body to be processed by etching using the patterned organic film as a mask.

Incidentally, this method can be performed in the same way as in the three layer resist process by using the silicon-containing resist middle layer film except that an inorganic hard mask is formed on the organic film instead of the silicon-containing resist middle layer film.

The inorganic hard mask selected from a silicon oxide film, a silicon nitride film, a silicon oxynitride film (SiON film), a titanium oxide film, and a titanium nitride film can be formed by a CVD method or an ALD method and the like. The method for forming a silicon nitride film is described in, for example, JP 2002-334869A and WO2004/066377. The inorganic hard mask preferably has a film thickness of 5 to 200 nm, more preferably 10 to 100 nm. As the inorganic hard mask, the SiON film, which has marked antireflective properties, is most preferably used. The temperature of a substrate can reach 300 to 500° C. when an SiON film is formed. Accordingly, the under layer film must be durable to temperatures ranging from 300 to 500° C. The organic film formed by using the inventive composition for forming an organic film has higher heat resistance and is durable to high temperatures ranging from 300 to 500° C., thereby making it possible to combine an inorganic hard mask formed by a CVD method or an ALD method and an organic film formed by a spin coating method.

[Four-Layer Resist Process Using Inorganic Hard Mask and Organic Antireflective Film]

As the patterning process by the four layer resist process using the composition for forming an organic film, the present invention can also be a patterning process in which an organic film is formed on a body to be processed by using the inventive composition for forming an organic film, an inorganic hard mask selected from a silicon oxide film, a silicon nitride film, a silicon oxynitride film, a titanium oxide film, and a titanium nitride film is formed on the organic film, an organic antireflective film is formed on the inorganic hard mask, a resist upper layer film is formed on the organic antireflective film by using a resist upper layer film material composed of a photoresist composition, a circuit pattern is formed in the resist upper layer film, the pattern is transferred to the organic antireflective film and the inorganic hard mask by etching using the circuit-patterned resist upper layer film as a mask, the pattern is transferred to the organic film by etching using the patterned inorganic hard mask as a mask, and the pattern is transferred to the body to be processed by etching using the patterned organic film as a mask.

Incidentally, this method can be performed in the same way as in the three layer resist process by using the inorganic hard mask except that the organic antireflective film (BARC) is formed between the inorganic hard mask and the resist upper layer film.

In particular, when a SiON film is used as the inorganic hard mask, it is possible to decrease reflection by virtue of the two-layer antireflective films of the SiON film and the BARC film, even in a liquid immersion exposure at a higher NA exceeding 1.0. Another merit of the formation of the BARC includes an effect of reducing footing of the resist upper layer film pattern just on the SiON film.

An example of the patterning process by a three layer resist process is shown in FIG. 2 (A) to (F). In the three layer resist process, as shown in FIG. 2 (A), on a layer to be processed 2 formed on a substrate 1, an organic film 3 is formed by using the inventive composition for forming an organic film, followed by forming a silicon-containing resist middle layer film 4, and forming a resist upper layer film 5 thereon. Then, as shown in FIG. 2 (B), the exposure area 6 of the resist upper layer film 5 is exposed, followed by performing post-exposure baking (PEB). Subsequently, as shown in FIG. 2 (C), a resist upper layer film pattern 5a is formed by development. Next, as shown in FIG. 2 (D), a silicon-containing resist middle layer film pattern 4a is formed by dry etching processing of the silicon-containing resist middle layer film 4 with fluorocarbon base gas using the resist upper layer film pattern 5a as a mask. Then, as shown in FIG. 2 (E), subsequent to removing the resist upper layer film pattern 5a, an organic film pattern 3a is formed by oxygen plasma etching of the organic film 3 using the silicon-containing resist middle layer film pattern 4a as a mask. Additionally, as shown in FIG. 2 (F), subsequent to removing the silicon-containing resist middle layer film pattern 4a, a pattern 2a is formed by etching processing of the layer to be processed 2 using the organic film pattern 3a as a mask.

In case of forming an inorganic hard mask, the process may be performed by changing the silicon-containing resist middle layer film 4 to the inorganic hard mask; and in case of forming a BARC, the process may be performed by forming the BARC between the silicon-containing resist middle layer film 4 and the resist upper layer film 5. It is possible to continuously perform etching of the BARC preceding to the etching of the silicon-containing resist middle layer film 4. It is also possible to perform etching of the BARC only, followed by etching of the silicon-containing resist middle layer film 4 after changing the etching apparatus, for example.

As described above, the inventive patterning process makes it possible to form a fine pattern on a substrate to be processed with high accuracy by a multilayer resist process.

EXAMPLE

Hereinafter, the present invention will be specifically described by showing Synthesis Examples, Comparative Synthesis Examples, Examples, and Comparative Examples, but the present invention is not limited thereto. Incidentally, as the molecular weight and dispersity, weight average molecular weight (Mw) and number average molecular weight (Mn) are determined in terms of polystyrene by gel permeation chromatography (GPC) using tetrahydrofuran as an eluent, and then the dispersity (Mw/Mn) was determined.

SYNTHESIS EXAMPLES: SYNTHESIS OF CURABLE ORGANIC COMPOUNDS

[Synthesis Example 1] Synthesis of Compound (A1)

In an $N_2$ atmosphere, to an ice-cooled mixed solution of 12.6 g of 1,3-diethynylbenzen, 36.0 g of 9-fluorenone, and 200 g of toluene, 24.7 g of potassium t-butoxide was added, and this was stirred for 3 hours in an ice bath. The reaction was stopped by adding water, and 200 mL of tetrahydrofuran was added thereto. This was washed with water and concentrated under reduced pressure, and then toluene was added thereto. The formed solid was filtered off, washed with toluene, and dried under reduced pressure to give 42.3 g of Compound (A1).

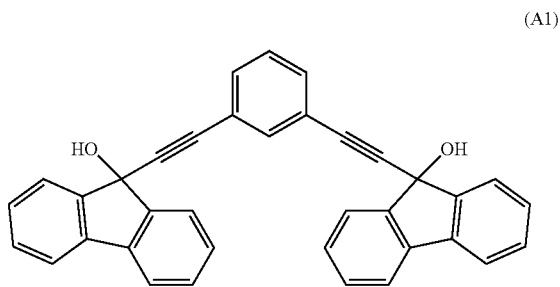 [SMILES: OC1(C#Cc2cccc(C#CC3(O)c4ccccc4-c4ccccc43)c2)c2ccccc2-c2ccccc21]

(A1)

Shown in the following are analytical results of IR and $^1$H NMR for the synthesized Compound (A1).

IR (D-ATR): ν=3310 (br), 3069, 3046, 3023, 1592, 1477, 1450, 1047, 1001, 791, 747, 726 cm$^{-1}$ $^1$H NMR (600 MHz, DMSO-d6): δ=7.78 (d, J=7.4 Hz, 4H), 7.70 (d, J=7.4 Hz, 4H), 7.43-7.40 (m, 4H), 7.37-7.34 (m, 7H), 7.32-7.29 (m, 1H), 6.70 (s, 2H) ppm.

[Synthesis Example 2] Synthesis of Compound (A2)

After mixing 9.7 g of Compound (A1), 0.5 g of N,N-dimethyl-4-aminopyridine, and 30 g of pyridine, the mixture was heated to 70° C. To the reaction mixture, 6.1 g of acetic anhydride was added, and this was heated to 80° C. and stirred for 4 hours. After cooling, the reaction was stopped by adding water. To this mixture, 100 mL of toluene and 100 mL of tetrahydrofuran were added. This was washed with water and concentrated under reduced pressure, and then hexane was added thereto. The formed solid was filtered off, washed with hexane, and dried under reduced pressure to give 9.4 g of Compound (A2).

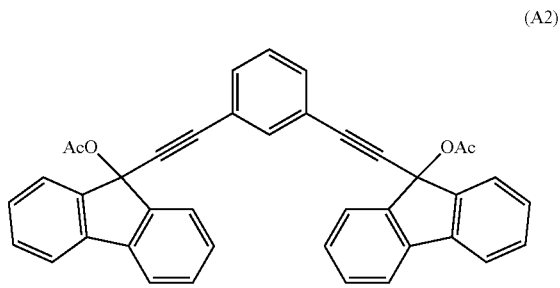 [SMILES: CC(=O)OC1(C#Cc2cccc(C#CC3(OC(C)=O)c4ccccc4-c4ccccc43)c2)c2ccccc2-c2ccccc21]

(A2)

Shown in the following are analytical results of IR and $^1$H NMR for the synthesized Compound (A2).

IR (D-ATR): ν=3065, 1745, 1592, 1476, 1450, 1231, 1209, 1050, 1008, 969, 794, 769, 755, 733 cm$^{-1}$ $^1$H NMR (600 MHz, DMSO-d6): δ=7.84 (d, J=7.6 Hz, 4H), 7.81 (d, J=7.6 Hz, 4H), 7.49-7.46 (m, 4H), 7.41-7.37 (m, 7H), 7.35-7.31 (m, 1H), 2.02 (s, 6H) ppm.

[Synthesis Example 3] Synthesis of Compound (A3)

In an N$_2$ atmosphere, to an ice-cooled mixed solution of 6.3 g of 1,3-diethynylbenzen and 100 g of tetrahydrofuran, 100 mL of 1 N magnesium ethyl bromide solution in tetrahydrofuran was added, and this was slowly warmed to room temperature. To this mixture, 20.2 g of thioxanthone was added, and this was heated to 40° C. and stirred for 24 hours. After cooling, the reaction was stopped by adding water. To this mixture, 200 mL of methyl isobutyl ketone was added. This was washed with water and concentrated under reduced pressure, and then hexane was added thereto. The formed solid was filtered off, washed with hexane, and dried under reduced pressure to give 17.1 g of the intended material (A3).

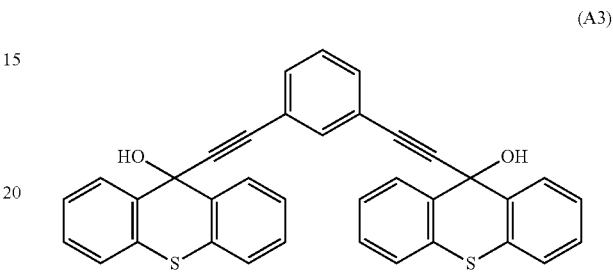

(A3)

Shown in the following are analytical results of IR and $^1$H NMR for the synthesized Compound (A3).

IR (D-ATR): ν=3299 (br), 3062, 3027, 1581, 1457, 1443, 1354, 1185, 1055, 992, 789, 755, 748, 736 cm$^{-1}$ $^1$H NMR (600 MHz, DMSO-d6): δ=7.98 (dd, J=7.8, 1.4 Hz, 4H), 7.54 (dd, J=7.8, 1.4 Hz, 4H), 7.39 (ddd, J=7.8, 7.8, 1.4 Hz, 4H), 7.33 (ddd, J=7.8, 7.8, 1.4 Hz, 4H), 7.30-7.28 (m, 5H), 7.21 (br s, 1H) ppm.

[Synthesis Example 4] Synthesis of Compound (A4)

After mixing 711.0 g of resorcinol, 33.2 g of potassium carbonate, and 90 g of N,N-dimethylformamide, the mixture was heated to 55° C. To the reaction mixture, 35.7 g of 80% propargyl bromide solution in toluene was slowly added dropwise, and this was heated and stirred at 55° C. for 17 hours. After cooling to room temperature, 150 g of toluene was added. This was washed with water and concentrated under reduced pressure to give 18.6 g of propargyl compound (B1).

In an N$_2$ atmosphere, to an ice-cooled mixed solution of 18.6 g of the propargyl compound (B1), 34.2 g of 9-fluorenone, and 100 g of tetrahydrofuran, 24.7 g of potassium t-butoxide was added, and this was stirred for 1 hour in an ice-bath. The reaction was stopped by adding saturated aqueous ammonium chloride solution. To this mixture, 200 mL of methyl isobutyl ketone was added. This was washed with water and concentrated under reduced pressure, and then the solvent was changed to propylene glycol monomethyl ether acetate to give Compound (A4) in a solid content of 47.4 g.

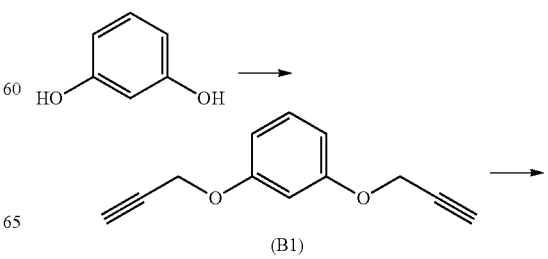

(B1)

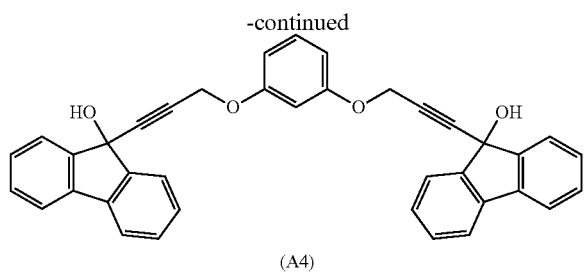

(A4)

Shown in the following are analytical results of ¹H NMR for the synthesized Compound (A4).

¹H NMR (600 MHz, DMSO-d6): δ=7.74 (d, J=7.3 Hz, 4H), 7.59 (d, J=7.3 Hz, 4H), 7.38 (ddd, J=7.3, 7.3, 1.4 Hz, 4H), 7.32 (ddd, J=7.3, 7.3, 1.4 Hz, 4H), 7.13 (dd, J=8.5, 8.5 Hz, 1H), 6.60 (s, 2H), 6.54-6.50 (m, 3H), 4.68 (s, 4H) ppm.

COMPARATIVE SYNTHESIS EXAMPLES: SYNTHESIS OF ORGANIC COMPOUNDS WITH HIGHER HEAT RESISTANCE

[Comparative Synthesis Example 1] Synthesis of Biphenyl Derivative (B2)

In an $N_2$ atmosphere, into a 5 L four-necked flask containing 26.4 g (1.09 mol) of weighed magnesium, a part of solution in which 168 g (0.54 mol) of 4,4'-dibromobiphenyl and 23.0 g (0.54 mol) of lithium chloride had been previously dissolved in 1,000 ml of dehydrated tetrahydrofuran (THF) was added so as to soak the magnesium. After adding small amount of dibromoethane to start the reaction, the remained THF solution was added dropwise for 3 hours while keeping the heat generation. After finishing the dropwise addition, 500 ml of THF was added, and this was aged for 8 hours under refluxing to prepare a Grignard reagent. After the bulk temperature was cooled to 55° C., a solution in which 150 g (0.83 mol) of 9-fluorenone had been previously dissolved in 400 ml of dehydrated THF was added dropwise for 2 hours. After the dropwise addition, the mixture was semi-aged for 5 hours under refluxing. The reaction was quenched by cooling the flask with an ice bath and adding 1,000 ml of saturated aqueous ammonium chloride solution and 1,000 ml of pure water. At this time, the solution turned to suspension, forming white precipitate. To the reaction mixture, 150 ml of methyl isobutyl ketone (MIBK) was added. This was poured into a separatory funnel as it was suspension, and the water layer was extracted. The water layer was washed with 500 ml of pure water in the separatory funnel, and concentrated under reduced pressure. After recrystallization from diisopropyl ether, the formed white crystal was filtered off and dried to give 109 g of Biphenyl derivative (B2) in a yield of 51.0%.

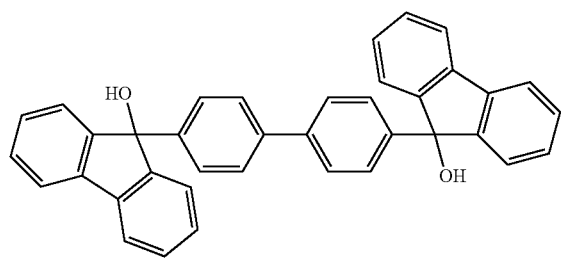

(B2)

Analysis results of Biphenyl derivative (B2):

IR (D-ATR): ν=3539, 3064, 3039, 1605, 1495, 1447, 1164, 1030, 909, 820, 771, 754, 736 cm⁻¹

¹H NMR (600 MHz, DMSO-d6): δ=6.34 (2H, —OH, s), 7.24 (4H, t), 7.27 (8H, d), 7.36 (4H, t-t), 7.45 (4H, d), 7.81 (4H, d) ppm ¹³C-NMR (150 MHz, DMSO-d₆): δ=82.44, 120.10, 124.66, 125.66, 126.28, 128.07, 128.51, 138.41, 139.14, 144.19, 151.23 ppm.

[Comparative Synthesis Example 2] Synthesis of Compound (A5)

In a 1 L three-necked flask, 40.3 g (78.4 mmol) of Biphenyl derivative (B2), 23.73 g (164.6 mmol) of 2-naphthol, and 240 ml of 1,2-dichloroethane were weighed. To this mixture, 7.3 ml of methanesulfonic acid was slowly added dropwise with stirring in an oil bath at 30° C. After finishing dropwise addition, the temperature of the oil bath was increased to 50° C., and the reaction was performed for 6 hours. The reaction mixture was left for cooling to room temperature, followed by dilution with 500 ml of MIBK, and insoluble matter was filtered. This was poured into a separatory funnel and washed with 300 ml of ultrapure water in the separatory funnel for 9 times. The organic layer was concentrated under reduced pressure, and 800 ml of THF was added to dissolve the residue, which was then recrystallized from 2,500 ml of hexane. Then, the crystal was filtered off and dried to give 51.6 g of Biphenyl derivative compound (A5) in a yield of 85.8%.

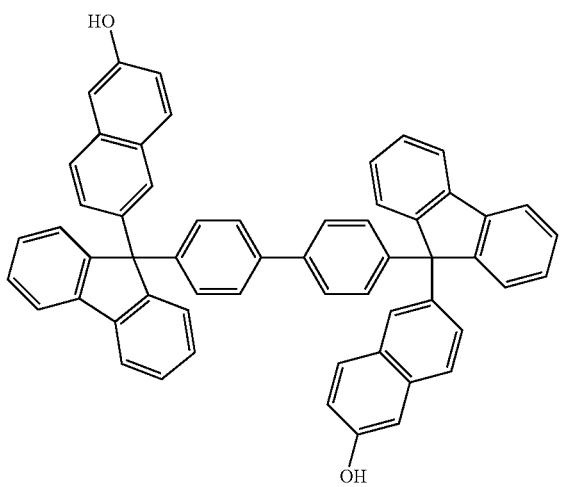

(A5)

Analysis results of Compound (A5):

IR (KBr): ν=3528, 3389, 3059, 3030, 1633, 1604, 1506, 1493, 1446, 1219, 1181, 750, 740 cm⁻¹

¹H NMR (600 MHz, DMSO-d6): δ=6.98 (2H, d-d), 7.05 (2H, s-d), 7.17 (4H, d), 7.24 (2H, d-d), 7.29 (4H, t), 7.38 (4H, t), 7.40 (2H, s), 7.45 (4H, d), 7.50 (6H, d), 7.58 (2H, d), 7.93 (4H, d), 9.72 (2H, —OH, s) ppm ¹³C-NMR (150 MHz, DMSO-d₆): δ=64.59, 108.35, 118.77, 120.58, 125.19, 126.11, 126.36, 126.62, 126.94, 127.16, 127.71, 127.88, 128.20, 129.35, 133.39, 138.14, 139.26, 139.59, 144.82, 150.56, 155.39 ppm.

[Comparative Synthesis Example 3] Synthesis of Compound (A6)

After mixing 7.7 g of Biphenyl derivative compound (A5), 3.0 g of potassium carbonate, and 40 g of N,N- dimethylformamide, the mixture was heated to 55° C. To the reaction mixture, 3.3 g of 80% propargyl bromide solution in toluene was slowly added dropwise, and this was heated and stirred at 55° C. for 14 hours. After cooling to room temperature, 150 g of toluene was added. This was washed with water and concentrated under reduced pressure to give 8.4 g of propargyl compound (A6).

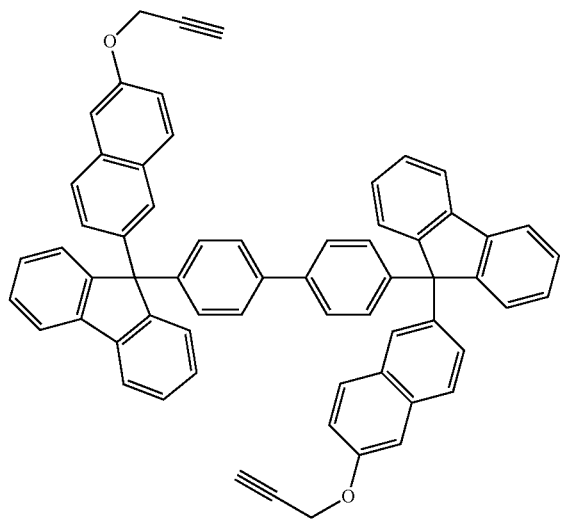

(A6)

The weight average molecular weight (Mw) and dispersity (Mw/Mn) were determined by GPC to give following results.
(A6): Mw=966, Mw/Mn=1.09

Synthesis of Compound (E1) Having Aromatic Ring as Partial Structure

After mixing 54.5 g of 9-phenyl-9-fluorenol and 200 g of 1,2-dichloroethane, the mixture was heated to 50° C. To the reaction mixture, 20.3 g of methanesulfonic acid was slowly added dropwise, and this was heated and stirred at 70° C. for 6 hours. After cooling to room temperature, 650 g of toluene was added. This was washed with water and concentrated under reduced pressure to give 60.7 g of Compound (E1).

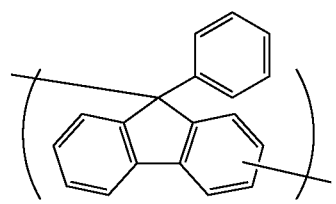

(E1)

The weight average molecular weight (Mw) and dispersity (Mw/Mn) were determined by GPC to give following results.
(E1): Mw=2700, Mw/Mn=1.39

Preparation of Organic Film Material (UDL-1 to 7, Comparative UDL-1 to 3)

Into a solution of 0.05% by mass of an acid generator (AG1) and 0.1% by mass of FC-4430 (manufactured by 3M Japan Limited) in propylene glycol monomethyl ether acetate (PGMEA), each of Compounds (A1) to (A6) and (E1) described above, together with 1,6-diacetoxyhexane (b.p.: 260° C.) (S1) or tripropylene glycol monomethyl ether (b.p.: 242° C.) (S2) as a high boiling point solvent were dissolved in each ratio shown in Table 1. This was filtrated through 0.1 μm filter made from fluororesin to prepare each Organic film material (UDL-1 to 7, Comparative UDL-1 to 3).

TABLE 1

| Composition for forming organic film | Compound (parts by mass) | Compound containing aromatic ring (parts by mass) | High boiling point solvent (parts by mass) | PGMEA (parts by mass) |
|---|---|---|---|---|
| UDL-1 | A1 (5) | — | — | 100 |
| UDL-2 | A2 (5) | — | — | 100 |
| UDL-3 | A3 (5) | — | — | 100 |
| UDL-4 | A4 (5) | — | — | 100 |
| UDL-5 | A1 (1) | E1 (4) | — | 100 |
| UDL-6 | A1 (5) | — | S1 (10) | 90 |
| UDL-7 | A1 (5) | — | S2 (10) | 90 |
| Comparative UDL-1 | A5 (5) | — | — | 100 |
| Comparative UDL-2 | A6 (5) | — | — | 100 |
| Comparative UDL-3 | A6 (1) | E1 (4) | — | 100 |

The following shows Acid generator (AG1).

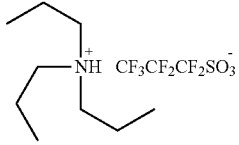

(AG1)

Example 1 Measurement of Solvent Resistance
(Examples 1-1 to 1-7, Comparative Examples 1-1 to 1-3)

Each organic film material (UDL-1 to 7, Comparative UDL-1 to 3) prepared in the above was applied onto a silicon substrate, and was baked at 450° C. for 60 seconds in a flow of nitrogen in which the oxygen concentration had been controlled to 0.2% or less. Then, the film thickness was measured. PGMEA solvent was dispensed thereonto and allowed to stand for 30 seconds, followed by spin drying and baking at 100° C. for 60 seconds to evaporate the PGMEA. The film thickness was measured, and the difference of film thickness before and after the PGMEA treatment was determined. The results are shown in Table 2.

TABLE 2

| | Composition for forming organic film | Film thickness after forming film: a (Å) | Film thickness after PGMEA treatment: b (Å) | b/a × 100 (%) |
|---|---|---|---|---|
| Example 1-1 | UDL-1 | 1155 | 1151 | 99.7 |
| Example 1-2 | UDL-2 | 1152 | 1147 | 99.6 |
| Example 1-3 | UDL-3 | 1156 | 1146 | 99.1 |
| Example 1-4 | UDL-4 | 1153 | 1146 | 99.4 |
| Example 1-5 | UDL-5 | 1157 | 1154 | 99.7 |

TABLE 2-continued

| Composition for forming organic film | Film thickness after forming film: a (Å) | Film thickness after PGMEA treatment: b (Å) | b/a × 100 (%) |
|---|---|---|---|
| Example 1-6 | UDL-6 | 1153 | 1152 | 99.9 |
| Example 1-7 | UDL-7 | 1157 | 1156 | 99.9 |
| Comparative Example 1-1 | Comparative UDL-1 | 1155 | 252 | 21.8 |
| Comparative Example 1-2 | Comparative UDL-2 | 1148 | 1137 | 99.0 |
| Comparative Example 1-3 | Comparative UDL-3 | 1148 | 350 | 30.5 |

As shown in Table 2, each of the inventive organic film materials (Examples 1-1 to 1-7) had a film remaining rate of 99% or more after the PGMEA treatment, which revealed that the crosslinking reaction occurred even in nitrogen atmosphere to bring sufficient solvent resistance. On the other hand, in Comparative Examples 1-1 and 1-3, sufficient solvent resistance was not attained such that each film remaining rate was less than 50% after the PGMEA treatment. These results have shown that the structure of the present invention, having a triple bond and a leaving group capable of forming a reactive cation, generates heat curing reaction to form a cured film with solvent resistance.

Example 2 Measurement of Solvent Resistance after Baking in the Atmosphere (Examples 2-1 to 2-7, Comparative Examples 2-1 to 2-3)

Each Composition for forming an organic film (UDL-1 to 7, Comparative UDL-1 to 3) prepared in the above was applied onto a silicon substrate, and was baked at 350° C. for 60 seconds in the atmosphere. Then, the film thickness was measured. PGMEA solvent was dispensed thereonto and allowed to stand for 30 seconds, followed by spin drying and baking at 100° C. for 60 seconds to evaporate the PGMEA. The film thickness was measured, and the difference of film thickness before and after the PGMEA treatment was determined. These results are shown in Table 3.

TABLE 3

| Composition for forming organic film | Film thickness after forming film: a (Å) | Film thickness after PGMEA treatment: b (Å) | b/a × 100 (%) |
|---|---|---|---|
| Example 2-1 | UDL-1 | 1157 | 1157 | 100.0 |
| Example 2-2 | UDL-2 | 1152 | 1147 | 99.6 |
| Example 2-3 | UDL-3 | 1153 | 1150 | 99.7 |
| Example 2-4 | UDL-4 | 1141 | 1140 | 99.9 |
| Example 2-5 | UDL-5 | 1142 | 1140 | 99.8 |
| Example 2-6 | UDL-6 | 1146 | 1145 | 99.9 |
| Example 2-7 | UDL-7 | 1157 | 1154 | 99.7 |
| Comparative Example 2-1 | Comparative UDL-1 | 1154 | 444 | 38.5 |
| Comparative Example 2-2 | Comparative UDL-2 | 1157 | 1147 | 99.1 |
| Comparative Example 2-3 | Comparative UDL-3 | 1150 | 570 | 49.6 |

As shown in Table 3, in the inventive composition for forming an organic film (Examples 2-1 to 2-7), each film remaining rate was 99% or more after the PGMEA treatment, showing that the crosslinking reaction also occurred in the atmosphere to attain sufficient solvent resistance. On the other hand, in Comparative Examples 2-1 and 2-3, sufficient solvent resistance was not attained such that the film remaining rates were less than 50% after the PGMEA treatment. These results have shown that the structure of the present invention, having a triple bond and a leaving group capable of forming a reactive cation, generates heat curing reaction even in the atmosphere to attain solvent resistance.

Example 3 Evaluation of Heat Resistance (Examples 3-1 to 3-7, Comparative Examples 3-1 to 3-3)

Each Composition for forming an organic film (UDL-1 to 7, Comparative UDL-1 to 3) described above was applied onto a silicon substrate, and was baked at 180° C. in the atmosphere to form a coated film with a thickness of 115 nm. The film thickness was measured. The substrate was additionally baked at 450° C. in a flow of nitrogen in which the oxygen concentration had been controlled to 0.2% or less, and the film thickness was measured (Examples 3-1 to 3-7, Comparative Examples 3-1 to 3-3). These results are shown in Table 4.

TABLE 4

| Composition for forming organic film | Film thickness baked at 180° C.: A (Å) | Film thickness baked at 450° C.: B (Å) | (B/A) × 100 (%) |
|---|---|---|---|
| Example 3-1 | UDL-1 | 1159 | 1156 | 99.7 |
| Example 3-2 | UDL-2 | 1157 | 1151 | 99.5 |
| Example 3-3 | UDL-3 | 1151 | 1141 | 99.1 |
| Example 3-4 | UDL-4 | 1151 | 1142 | 99.2 |
| Example 3-5 | UDL-5 | 1152 | 1141 | 99.0 |
| Example 3-6 | UDL-6 | 1150 | 1142 | 99.3 |
| Example 3-7 | UDL-7 | 1155 | 1153 | 99.8 |
| Comparative Example 3-1 | Comparative UDL-1 | 1150 | 246 | 21.4 |
| Comparative Example 3-2 | Comparative UDL-2 | 1154 | 1011 | 87.6 |
| Comparative Example 3-3 | Comparative UDL-3 | 1149 | 270 | 23.5 |

As shown in Table 4, in the inventive organic film material (Examples 3-1 to 3-7), each decrease in film thickness was less than 1% even after baking at 450° C., showing that the film thickness was maintained after the treatment at 450° C. to prove the higher heat resistance of the inventive organic film material. On the other hand, in Comparative Examples 3-1 and 3-3, the film thicknesses were decreased largely compared to the inventive organic film materials. It has been found that the inventive organic film material shows excellent heat resistance in an inert gas atmosphere since each film thickness after baking at 180° C. was maintained after baking at 450° C. in a nitrogen atmosphere.

Example 4 Evaluation of Gap Filling Characteristics (Examples 4-1 to 4-7, Comparative Examples 4-1 to 4-3)

Each organic film material (UDL-1 to 7, Comparative UDL-1 to 3) described above was applied onto an $SiO_2$ wafer substrate having a dense hole pattern as shown in FIG. 3 (hole diameter: 0.16 μm, hole depth: 0.50 μm, the distance between the centers of two adjacent holes: 0.32 μm). This was baked at 450° C. for 60 seconds by using a hot plate in a flow of nitrogen in which the oxygen concentration had been controlled to 0.2% or less to form an organic film 8. The substrate used in this Example was a basis substrate 7 ($SiO_2$ wafer substrate) having a dense hole pattern shown in FIG. 3 (G) (bird's-eye view) and (H) (cross sectional view).

Each cross sectional profile of the obtained wafer substrates were observed through scanning electron microscope (SEM) to determine whether the holes were filled with the organic film without having void therein. The results are shown in Table 5. In case of using an organic film material with inferior gap filling characteristics, voids are supposed to form in the holes in this evaluation. In case of using an organic film material with good gap filling characteristics, the holes will be filled with the organic film without forming a void in this evaluation as shown in FIG. 3 (I). The results are shown in Table 5.

TABLE 5

|  | Composition for forming organic film | Void |
| --- | --- | --- |
| Example 4-1 | UDL-1 | Non |
| Example 4-2 | UDL-2 | Non |
| Example 4-3 | UDL-3 | Non |
| Example 4-4 | UDL-4 | Non |
| Example 4-5 | UDL-5 | Non |
| Example 4-6 | UDL-6 | Non |
| Example 4-7 | UDL-7 | Non |
| Comparative Example 4-1 | Comparative UDL-1 | Exist |
| Comparative Example 4-2 | Comparative UDL-2 | Exist |
| Comparative Example 4-3 | Comparative UDL-3 | Exist |

As shown in Table 5, it was confirmed that the inventive composition for forming an organic film (Examples 4-1 to 4-7) brought excellent gap filling characteristics such that the hole pattern was successfully filled without forming a void. On the other hand, it was confirmed that Comparative Examples 4-1 to 4-3 caused voids, thereby failing to attain good gap filling characteristics. These results have shown that the inventive composition for forming an organic film ensures heat resistance to improve the gap filling characteristics due to the inventive compound of a structure having a triple bond and a leaving group capable of forming a reactive cation. On the other hand, Comparative Examples 4-1 to 4-3 failed to obtain good gap filling characteristics in nitrogen atmosphere, causing voids due to insufficient heat resistance.

Example 5 Evaluation of Planarizing Characteristics (Examples 5-1 to 5-7, Comparative Examples 5-1 to 5-3)

Each Composition for forming an organic film (UDL-1 to 7; Comparative UDL-1 to 3) was applied onto a basis substrate 9 (SiO$_2$ wafer substrate) having a large isolated trench pattern shown in FIG. 4 (FIG. 4 (F), trench width: 10 μm, trench depth: 0.10 μm). This was baked at 450° C. for 60 seconds in a flow of nitrogen in which the oxygen concentration had been controlled to 0.2% or less. The step of the organic film 10 between the trench portion and non-trench portion (delta 10 in FIG. 4 (K)) was observed by using NX10 Atomic Force Microscope (AFM) manufactured by Park Systems. The results are shown in Table 6. In this evaluation, smaller step means better planarizing characteristics. Incidentally, this evaluation adopted severe conditions to evaluate planarizing characteristics such that a trench pattern with the depth of 0.10 μm was planarized by using the composition for forming an organic film with the ordinal film thickness of 0.2 μm. The results are shown in Table 6.

TABLE 6

|  | Composition for forming organic film | Step (nm) |
| --- | --- | --- |
| Example 5-1 | UDL-1 | 55 |
| Example 5-2 | UDL-2 | 60 |
| Example 5-3 | UDL-3 | 60 |
| Example 5-4 | UDL-4 | 50 |
| Example 5-5 | UDL-5 | 55 |
| Example 5-6 | UDL-6 | 35 |
| Example 5-7 | UDL-7 | 35 |
| Comparative Example 5-1 | Comparative UDL-1 | 90 |
| Comparative Example 5-2 | Comparative UDL-2 | 90 |
| Comparative Example 5-3 | Comparative UDL-3 | 90 |

As shown in Table 6, it was confirmed that the inventive composition for forming an organic film (Examples 5-1 to 5-7) excelled in planarizing characteristics such that each organic film had a smaller step between the trench portion and non-trench portion compared to those of Comparative Examples 5-1 to 5-3. These results have also shown superiority in planarizing characteristics of the inventive compound with the structure having a triple bond and a leaving group capable of forming a reactive cation. In comparison between Examples 5-6 to 5-7, which contained high boiling point solvent, and Example 5-1 without containing the same, it was found that the planarizing characteristics was more improved by the addition of high boiling point solvent.

Example 6 Patterning Test (Examples 6-1 to 6-7, Comparative Examples 6-1 to 6-3)

Each Composition for forming an organic film (UDL-1 to 7; Comparative UDL-1 to 3) described above was applied onto a silicon wafer substrate having an SiO$_2$ film with the thickness of 300 nm formed thereon. This was baked at 450° C. for 60 seconds in a flow of nitrogen in which the oxygen concentration had been controlled to 0.2% or less to form an organic film (resist under layer film). A CVD-SiON hard mask was formed thereon. Additionally, an organic antireflective film material (ARC-29A, manufactured by NISSAN CHEMICAL INDUSTRIES, LTD.) was applied and baked at 210° C. for 60 seconds to form an organic antireflective film with the film thickness of 80 nm. A single layer resist for ArF of a resist upper layer film material was applied thereonto, and baked at 105° C. for 60 seconds to form a photoresist film with the film thickness of 100 nm. A liquid immersion top coat composition (TC-1) was applied on the photoresist film, and baked at 90° C. for 60 seconds to form a top coat with the film thickness of 50 nm.

The resist upper layer film material (single layer resist for ArF) was prepared by dissolving Polymer (RP1), an acid generator (PAG1), and a basic compound (Amine1) in each ratio shown in Table 7 into a solvent containing 0.1% by mass of FC-4430 (manufactured by 3M Japan Limited), followed by filtration through 0.1 μm filter made from fluororesin.

TABLE 7

|  | Polymer (parts by mass) | Acid generator (parts by mass) | Basic compound (parts by mass) | Solvent (parts by mass) |
| --- | --- | --- | --- | --- |
| Single layer resist for ArF | PR1 (100) | PAG1 (6.6) | Amine1 (0.8) | PEGMEA (2500) |

The following shows the polymer (RP1), the acid generator (PAG1), and the basic compound (Amine1) used herein.

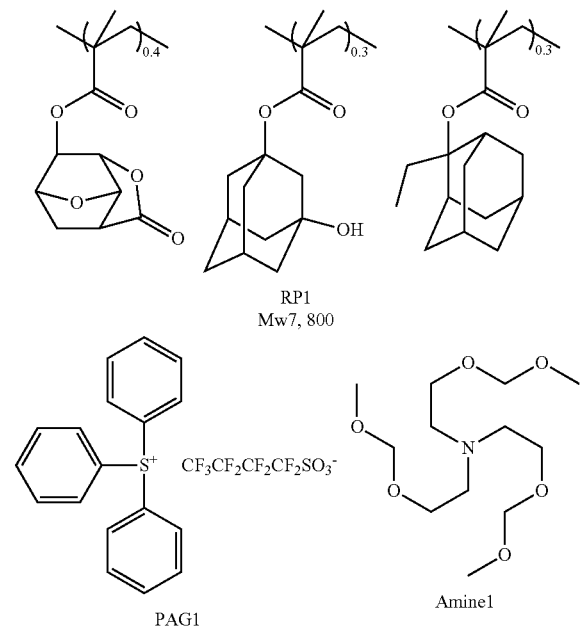

RP1
Mw7,800

PAG1

Amine1

The liquid immersion top coat material (TC-1) was prepared by dissolving the top coat polymer (PP1) into an organic solvent in a ratio described in Table 8, followed by filtration through 0.1 μm filter made from fluororesin.

TABLE 8

| | Polymer (parts by mass) | Organic solvent (parts by mass) |
|---|---|---|
| TC-1 | PP1 (100) | diisoamyl ether (2700) 2-methyl-1-butanol (270) |

The following is the polymer (PP1) used herein.

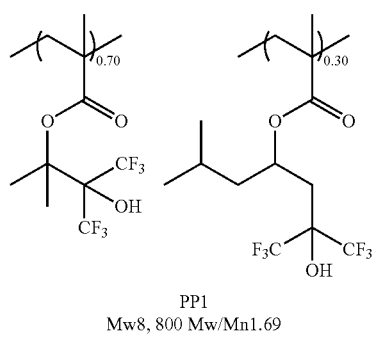

PP1
Mw8,800 Mw/Mn1.69

Then, the film was exposed by using ArF liquid immersion exposure apparatus (NSR-S610C manufactured by Nikon Corporation, NA: 1.30, σ: 0.98/0.65, 35° dipole s polarizing illumination, 6% half-tone phase shift mask), baked at 100° C. for 60 seconds (PEB), and developed with 2.38% by mass aqueous tetramethylammonium hydroxide (TMAH) solution for 30 seconds to obtain 55 nm 1:1 positive-type line-and-space pattern.

Subsequently, etching processing was performed by using an etching apparatus Telius manufactured by Tokyo Electron Limited such that the organic antireflective film and the CVD-SiON hard mask were subjected to dry etching using the resist pattern as a mask to form a hard mask pattern, the organic film was subjected to etching using the hard mask pattern as a mask to form an organic film pattern, and the $SiO_2$ film was subjected to etching processing by using the obtained organic film pattern as a mask. The etching conditions are as shown below.

Transcription conditions of the resist pattern to the SiON hard mask.

| | |
|---|---|
| Chamber pressure | 10.0 Pa |
| RF power | 1,500 W |
| $CF_4$ gas flow rate | 75 sccm |
| $O_2$ gas flow rate | 15 sccm |
| Time | 15 sec |

Transcription conditions of the hard mask pattern to the organic film.

| | |
|---|---|
| Chamber pressure | 2.0 Pa |
| RF power | 500 W |
| Ar gas flow rate | 75 sccm |
| $O_2$ gas flow rate | 45 sccm |
| Time | 120 sec |

Transcription conditions of the organic film pattern to the $SiO_2$ film.

| | |
|---|---|
| Chamber pressure | 2.0 Pa |
| RF power | 2,200 W |
| $C_5F_{12}$ gas flow rate | 20 sccm |
| $C_2F_6$ gas flow rate | 10 sccm |
| Ar gas flow rate | 300 sccm |
| $O_2$ gas flow rate | 60 sccm |
| Time | 90 sec |

Each pattern cross-section was observed by an electron microscope (S-4700) manufactured by Hitachi, Ltd., and the results are shown in Table 9.

TABLE 9

| | Composition for forming organic film | Pattern profile after substrate transcription etching |
|---|---|---|
| Example 6-1 | UDL-1 | Perpendicular |
| Example 6-2 | UDL-2 | Perpendicular |
| Example 6-3 | UDL-3 | Perpendicular |
| Example 6-4 | UDL-4 | Perpendicular |
| Example 6-5 | UDL-5 | Perpendicular |
| Example 6-6 | UDL-6 | Perpendicular |
| Example 6-7 | UDL-7 | Perpendicular |
| Comparative Example 6-1 | Comparative UDL-1 | Pattern collapse |
| Comparative Example 6-2 | Comparative UDL-2 | Perpendicular |
| Comparative Example 6-3 | Comparative UDL-3 | Pattern collapse |

As shown in Table 9, it was confirmed that the inventive composition for forming an organic film is favorably used for fine processing by a multilayer resist process such that each of the resist upper layer film patterns was finally transferred to the substrate favorably in the results of the inventive composition for forming an organic film (Examples 6-1 to 6-7). On the other hand, Comparative Examples 6-1 and 6-3 failed to obtain a good pattern such that pattern collapse was caused in the patterning process since the heat resistance was insufficient and the curing was insufficient in nitrogen atmosphere as shown in Example 1. In Comparative Example 6-2, a pattern could be formed, but the heat resistance was insufficient.

Example 7 Patterning Test (Examples 7-1 to 7-7, Comparative Examples 7-1 to 7-3)

By the same method as in Example 6, forming of a laminate, patterning, and dry etching were performed except that each Composition for forming an organic film (UDL-1 to 7; Comparative UDL-1 to 3) was applied onto an $SiO_2$ wafer substrate having a trench pattern (trench width: 10 μm, trench depth: 0.10 μm), and was baked at 450° C. for 60 seconds in a flow of nitrogen in which the oxygen concentration had been controlled to 0.2% or less. Each obtained pattern profile was observed. The results are shown in Table 10.

TABLE 10

|  | Composition for forming organic film | Pattern profile after substrate transcription etching |
| --- | --- | --- |
| Example 7-1 | UDL-1 | Perpendicular |
| Example 7-2 | UDL-2 | Perpendicular |
| Example 7-3 | UDL-3 | Perpendicular |
| Example 7-4 | UDL-4 | Perpendicular |
| Example 7-5 | UDL-5 | Perpendicular |
| Example 7-6 | UDL-6 | Perpendicular |
| Example 7-7 | UDL-7 | Perpendicular |
| Comparative Example 7-1 | Comparative UDL-1 | Pattern collapse |
| Comparative Example 7-2 | Comparative UDL-2 | Pattern collapse |
| Comparative Example 7-3 | Comparative UDL-3 | Pattern collapse |

As shown in Table 10, in the inventive compositions for forming an organic film (Examples 7-1 to 7-7), each resist upper layer film pattern was finally transferred to the substrate favorably to confirm that the inventive composition for forming an organic film is favorably used for fine processing by a multilayer resist process. On the other hand, in Comparative Example 7-2, even the cured film having solvent resistance caused pattern collapse in patterning processing due to the ill gap filling of pattern, failing to obtain a favorable pattern finally.

As described above, it has revealed that the inventive composition for forming an organic film containing the inventive compound can be cured in a condition for forming a film in an inert gas not only in the air to have excellent dry etching durability as well as heat resistance at a temperature of 450° C. or more and higher gap filling/planarizing characteristics even in an inert gas that does not contain oxygen, thereby being a very useful composition as an organic film material used for a multilayer resist process, and the inventive patterning process using the same is capable of forming a fine pattern with highly accuracy even when the substrate to be processed is a stepped substrate.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A composition for forming an organic film, comprising:
   (A) a compound shown by the following general formula (1-2), and
   (B) an organic solvent,

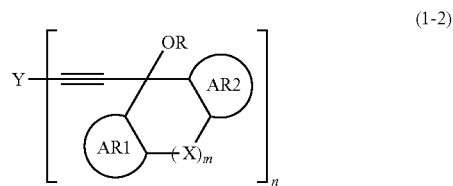

(1-2)

wherein AR1 and AR2 each represent a benzene ring, a naphthalene ring, or a pyridine ring optionally having an alkoxy group, an alkenyloxy group, or an aryloxy group having 1 to 30 carbon atoms; "m" is 1; AR1 and AR2 form a bridged structure in which the aromatic rings of AR1 and AR2 are bonded with each other through X; X represents a single bond or any of groups shown by the following formulae (3);

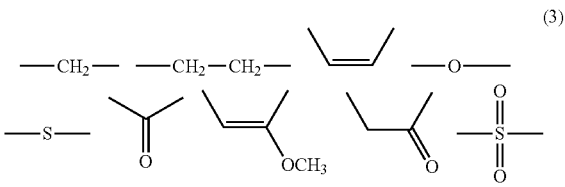

(3)

Y represents an n-valent organic group having 1 to 30 carbon atoms in which n=2 to 4 or an organic group-containing polymer having n-pieces of repeating units in which 2≤n≤1000; and R represents a hydrogen atom or a monovalent organic group having 1 to 30 carbon atoms.

2. The composition for forming an organic film according to claim 1, further comprising one or more components selected from the group consisting of (C) an acid generator, (D) a surfactant, (E) a compound having a partial structure of an aromatic ring other than the compound of the component (A), and (F) a plasticizer.

3. The composition for forming an organic film according to claim 2, wherein the component (E) has a weight average molecular weight of 500 to 100,000.

4. A substrate for manufacturing a semiconductor apparatus, comprising a basis substrate and an organic film formed on the basis substrate, the organic film being a cured material of the composition for forming an organic film according to claim 1.

5. A method for forming an organic film applied in a semiconductor apparatus manufacturing process, the method comprising:
   applying the composition for forming an organic film according to claim 1 on a body to be processed by spin coating; and
   heating the body to be processed, on which the composition for forming an organic film has been applied, at a temperature of 50° C. or more and 600° C. or less for 5 to 7200 seconds in an inert gas atmosphere to form a cured film.

6. A method for forming an organic film applied in a semiconductor apparatus manufacturing process, the method comprising:

applying the composition for forming an organic film according to claim 1 on a body to be processed by spin coating;

heating the body to be processed, on which the composition for forming an organic film has been applied, at a temperature of 50° C. or more and 300° C. or less for 5 to 600 seconds in air to form a coating film, and heating the body to be processed, on which the coating film has been formed, subsequently at a temperature of 200° C. or more and 600° C. or less for 10 to 7200 seconds in an inert gas atmosphere to form a cured film.

7. The method for forming an organic film according to claim 5, wherein the inert gas has an oxygen content of 1% or less.

8. The method for forming an organic film according to claim 5, wherein the body to be processed has steps or a structure with a height of 30 nm or more.

9. A patterning process comprising:

forming an organic film on a body to be processed from the composition for forming an organic film according to claim 1;

forming a silicon-containing resist middle layer film on the organic film from a resist middle layer film material containing silicon;

forming a resist upper layer film on the silicon-containing resist middle layer film from a resist upper layer film material composed of a photoresist composition;

forming a circuit pattern in the resist upper layer film;

transferring the pattern to the silicon-containing resist middle layer film by etching using the resist upper layer film having the formed circuit pattern as a mask;

transferring the pattern to the organic film by etching using the silicon-containing resist middle layer film having the transferred pattern as a mask; and transferring the pattern to the body to be processed by etching using the organic film having the transferred pattern as a mask.

10. A patterning process comprising:

forming an organic film on a body to be processed from the composition for forming an organic film according to claim 1;

forming a silicon-containing resist middle layer film on the organic film from a resist middle layer film material containing silicon;

forming an organic antireflective film on the silicon-containing resist middle layer film;

forming a resist upper layer film on the organic antireflective film from a resist upper layer film material composed of a photoresist composition to form a four-layered film structure;

forming a circuit pattern in the resist upper layer film;

transferring the pattern to the organic antireflective film and the silicon-containing resist middle layer film by etching using the resist upper layer film having the formed circuit pattern as a mask;

transferring the pattern to the organic film by etching using the silicon-containing resist middle layer film having the transferred pattern as a mask; and transferring the pattern to the body to be processed by etching using the organic film having the transferred pattern as a mask.

11. A patterning process comprising:

forming an organic film on a body to be processed from the composition for forming an organic film according to claim 1;

forming an inorganic hard mask selected from a silicon oxide film, a silicon nitride film, a silicon oxynitride film, a titanium oxide film, and a titanium nitride film on the organic film;

forming a resist upper layer film on the inorganic hard mask from a resist upper layer film material composed of a photoresist composition;

forming a circuit pattern in the resist upper layer film;

transferring the pattern to the inorganic hard mask by etching using the resist upper layer film having the formed circuit pattern as a mask;

transferring the pattern to the organic film by etching using the inorganic hard mask having the transferred pattern as a mask; and transferring the pattern to the body to be processed by etching using the organic film having the transferred pattern as a mask.

12. A patterning process comprising:

forming an organic film on a body to be processed from the composition for forming an organic film according to claim 1;

forming an inorganic hard mask selected from a silicon oxide film, a silicon nitride film, a silicon oxynitride film, a titanium oxide film, and a titanium nitride film on the organic film;

forming an organic antireflective film on the inorganic hard mask;

forming a resist upper layer film on the organic antireflective film from a resist upper layer film material composed of a photoresist composition to form a four-layered film structure;

forming a circuit pattern in the resist upper layer film;

transferring the pattern to the organic antireflective film and the inorganic hard mask by etching using the resist upper layer film having the formed circuit pattern as a mask;

transferring the pattern to the organic film by etching using the inorganic hard mask having the transferred pattern as a mask; and transferring the pattern to the body to be processed by etching using the organic film having the transferred pattern as a mask.

13. The patterning process according to claim 11, wherein the inorganic hard mask is formed by a CVD method or an ALD method.

14. The patterning process according to claim 9, wherein the circuit pattern is formed by a photolithography with a wavelength ranging from 10 nm to 300 nm, a direct drawing by electron beam, a nanoimprinting, or a combination thereof.

15. The patterning process according to claim 9, wherein the circuit pattern is developed by alkaline development or development with an organic solvent.

16. The patterning process according to claim 9, wherein the body to be processed is a semiconductor apparatus substrate or the semiconductor apparatus substrate coated with any of a metal film, a metal carbide film, a metal oxide film, a metal nitride film, a metal oxycarbide film, and a metal oxynitride film.

17. The patterning process according to claim 16, wherein the body to be processed contains silicon, titanium, tungsten, hafnium, zirconium, chromium, germanium, copper, silver, gold, aluminum, indium, gallium, arsenic, palladium, iron, tantalum, iridium, cobalt, manganese, molybdenum, or an alloy thereof.

* * * * *